United States Patent
Liu et al.

(10) Patent No.: US 7,608,622 B2
(45) Date of Patent: Oct. 27, 2009

(54) IMIDAZO[4,5-B]PYRAZINONE INHIBITORS OF PROTEIN KINASES

(75) Inventors: Jian Liu, Plainsboro, NJ (US);
Raymond J. Patch, Yardley, PA (US);
Mark R. Player, Phoenixville, PA (US);
Huaping Hu, Pennington, NJ (US)

(73) Assignee: Janssen Pharmaceutica NV (BE)

( * ) Notice: Subject to any disclaimer, the term of this patent is extended or adjusted under 35 U.S.C. 154(b) by 478 days.

(21) Appl. No.: 11/233,725

(22) Filed: Sep. 23, 2005

(65) Prior Publication Data

US 2006/0106022 A1    May 18, 2006

Related U.S. Application Data

(60) Provisional application No. 60/612,902, filed on Sep. 24, 2004, provisional application No. 60/692,122, filed on Jun. 20, 2005.

(51) Int. Cl.
| | |
|---|---|
| *A01N 43/58* | (2006.01) |
| *A61K 31/50* | (2006.01) |
| *A01N 43/60* | (2006.01) |
| *A61K 31/495* | (2006.01) |
| *C07D 471/00* | (2006.01) |
| *C07D 487/00* | (2006.01) |
| *C07D 491/00* | (2006.01) |
| *C07D 495/00* | (2006.01) |
| *C07D 497/00* | (2006.01) |

(52) U.S. Cl. ................................ 514/249; 544/350

(58) Field of Classification Search ................... None
See application file for complete search history.

(56) References Cited

FOREIGN PATENT DOCUMENTS

GB    2400101 A    10/2004

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
International Search Report re: PCT/US05/34395 dated May 3, 2006.

* cited by examiner

*Primary Examiner*—James O Wilson
*Assistant Examiner*—Jeffrey H Murray

(57) ABSTRACT

The invention is directed to compounds of Formula I:

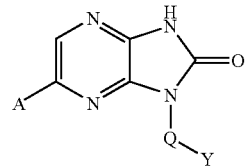

wherein Q, Y, A are set forth in the specification, as well as solvates, hydrates, tautomers or pharmaceutically acceptable salts thereof, that inhibit protein kinases, especially Aurora-1, Aurora-2 and Aurora-3 kinases.

6 Claims, No Drawings

IMIDAZO[4,5-B]PYRAZINONE INHIBITORS OF PROTEIN KINASES

CROSS-REFERENCE TO RELATED APPLICATIONS

This application claims priority to U.S. Application No. 60/612,902 filed on Sep. 24, 2004 and of U.S. Application No. 60/692,122 filed on Jun. 20, 2005. The content of both documents is incorporated herein by reference.

FIELD OF THE INVENTION

The invention relates to novel substituted 1,3-dihydro-imidazo[4,5-b]pyrazin-2-ones that function as protein kinase inhibitors. More particularly, the invention relates, to 1,6-disubstituted-1,3-dihydro-imidazo[4,5-b]pyrazin-2-ones, and compositions thereof, that function as inhibitors of Aurora-1, Aurora-2 and Aurora-3 kinases. The invention further relates to methods of treatment, to the use as a medicine and more in particular to the use in the treatment of cancers.

BACKGROUND OF THE INVENTION

Protein kinases are enzymes that serve as key components of signal transduction pathways by catalyzing the transfer of the terminal phosphate from ATP to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer, inflammation and diabetes.

Protein kinases can be divided into two classes: those, which preferentially phosphorylate tyrosine residues (protein tyrosine kinases) and those, which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation-processes, which ultimately results in oncogene transcription. Breast, colorectal and prostate cancers have been linked to this family of receptors.

FLT-3 (FMS-like tyrosine kinase 3) is a member of the receptor tyrosine kinase family that includes PDGFR, c-kit, and c-fms. FLT-3 kinase is expressed mainly by early myeloid and lymphoid progenitor cells and is involved in the proliferation, differentiation, and apoptosis of hematopoietic cells. FLT-3 kinase is activated by FLT-3 ligand, which upon binding to the receptor causes dimerization and autophosphorylation and subsequent activation of the kinase domain, which subsequently then activates the phosphoinositol-3-kinase (PI3K), STAT and RAS signal transduction pathways.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Insulin receptor ("IR") and insulin-like growth factor I receptor ("IGF-R") are structurally and functionally related but exert distinct biological effects. IGF-R expression has been associated with breast cancer.

c-Met serves as the high affinity receptor for hepatocyte growth factor (HGF), signalling through which leads to proliferation, scattering and branching morphogenesis. Overexpression of c-Met has been linked to a number of cancers including hereditary papillary renal carcinomas, ovarian cancer, and head and neck squamous cell carcinomas.

Fibroblast growth factor ("FGR") receptors consist of four receptors that are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF, flt and KDR, are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Cyclin-dependent kinases ("CDK") are serine/threonine kinases, which are key regulatory components cell cycle entry and progression. Each CDK is associated with a regulatory subunit (cyclin) and together each complex mediates a particular stage of the cell cycle. Inhibitors of CDKs have potential uses in the treatment of cancer.

Mitogen-activated protein ("MAP") kinases are serine/threonine kinases that can be divided into three groups in mammalian cells: extracellular signal-regulated kinase (ERK), c-jun N-terminal kinase (JNK), and p38 MAP kinase. p38 MAP kinases play key roles in cellular responses to external stress signals, while inhibitors have anti-inflammatory roles in key animal models of inflammation. The ERK pathway is an important determinant in the control of cell growth, cell differentiation and cell survival. This pathway is up-regulated in human tumors and represents a target for anticancer therapy.

Aurora kinases are a family of serine/threonine kinases that are important regulators of the mitotic cellular division process (Bischoff J R, Plowman G D: Trends Cell Biol. 1999 November; 9(11): 454-9 and Carmena M, Eamnshaw W C: Nat Rev Mol Cell Biol. 2003 November; 4(11): 842-54). Expression of all Aurora kinases peaks during the G2 and M phases of the cell cycle, while being low in cells at rest. Inhibitors of the Aurora family of kinases may block growth of all cancer types (Katayama H4, Brinkley W R, Sen S: Cancer Metastasis Rev. 2003 December; 22(4): 451-64 and Harrington E A, Bebbington D, et al.: Nat Med. 2004 March; 10(3): 262-7).

Members of the Aurora family of kinases [Aurora-1 ("A"), Aurora-2 ("B") and Aurora-3 ("C")] are highly homologous, especially within the C-terminal domain, although they differ in the length and sequence in the N-terminal domain (Bischoff J R, Anderson L, et al.: EMBO J. 1998 Jun. 1; 17(11):

3052-65 and Giet R, Prigent C: J Cell Sci. 1999 November; 112 (Pt 21): 3591-601). As the three Aurora kinases have nearly identical ATP binding sites, inhibitors, which bind at this location, may be expected to inhibit all three Aurora subtypes.

Aurora-1 is localized in the centrosome and in the spindle midzone and midbody (Sugimoto K, Urano T, et al.: Cell Struct Funct. 2002 December; 27(6): 457-67). Aurora-1 plays a critical role in mitotic spindle formation and centrosome maturation, which ensures accurate separation of chromosomes into each daughter cell (Giet R, McLean D, et al.: J. Cell Biol. 2002 Feb. 4; 156(3): 437-51). Overexpression of Aurora-1 transforms fibroblasts and yields aneuploid cells that contain multiple centrosomes and multipolar spindles (Giet R, Prigent C: J Cell Sci. 1999 November; 112 (Pt 21): 3591-601). Aurora-1 maps to 20q13.2 in humans, a region that is amplified in some primary tumors (Tanner M M, Grenman S, et al.: Clin Cancer Res. 2000 May; 6(5): 1833-9). Overexpression of the Aurora-1 kinases has been detected in a wide range of tumor types including: colorectal, gastric, ovarian and breast (Sakakura C, Hagiwara A, et al.: Br J Cancer. 2001 Mar. 23; 84(6): 824-31; Takahashi T, Futamura M, et al.: Jpn J Cancer Res. 2000 October; 91(10): 1007-14; Gritsko T M, Coppola D, et al.: Clin Cancer Res. 2003 April; 9(4): 1420-6 and Tanaka T, Kimura M, et al.: Cancer Res. 1999 May 1; 59(9): 2041-4).

Aurora-2 kinase is a protein associated with chromosomes that is important for chromosomal bioriention on the mitotic spindle and in the regulation of kinetochore-microtubule interactions (Ditchfield C, Johnson V L, et al.: J. Cell Biol. 2003 Apr. 28; 161(2): 267-80). Aurora-2 kinase is overexpressed in various tumor cell types and increases in line with the Duke stage of primary colorectal cancer (Katayama H, Ota T, et al.: J Natl Cancer Inst. 1999 Jul. 7; 91(13): 1160-2).

Aurora-3 kinase is collocated to the testis in normal tissue, but has been shown to be overexpressed in a high percentage of colorectal cancers (Takahashi T, Futamura M, et al.: Jpn J Cancer Res. 2000 October; 91(10): 1007-14). Aurora-3 kinase exhibits a centrosomal location from anaphase through telophase.

Small molecule kinase inhibitors of the Aurora kinases have been described, one of which inhibited the proliferation of a wide range of tumor cell types and suppressed tumor growth in vivo (Ditchfield C, Johnson V L, et al.: J. Cell Biol. 2003 Apr. 28; 161(2): 267-80; Harrington E A, Bebbington D, et al.: Nat Med. 2004 March; 10(3): 262-7 and Hauf S, Cole R W, et al.: J. Cell Biol. 2003 Apr. 28; 161(2): 281-94). The cell death was due to apotosis and was associated with an inhibition of Ser10 phosphorylation on Histone H3, which is a downstream target of the Aurora kinases.

RELATED ART

International patent application WO 88/03025, published on May 5, 1988, describes heterocyclic substituted bicycloureas having cardiotonic activity.

European Patent Application EP 0 385 850, published on Sep. 5, 1990, describes derivatives of benzimidazoles and azabenzimidazoles in the treatment of cardiovascular diseases and in duodenal ulcers.

European Patent Application EP 0 785 201, published on Jul. 23, 1997, describes cyclopentanopyridyl-oxazolidinone derivatives having antibacterial activity.

International patent application WO 00/50419, published on Aug. 31, 2000, describes substituted bicyclic heterocycles and the use thereof as thrombin inhibitors.

International patent application WO 03/007945, published on Jan. 30, 2003, describes viral polymerase inhibitors.

International patent application WO 03/014377, published on Feb. 20, 2003, describes probes for direct binding assay for identifying inhibitors of HCV polymerase.

International patent application WO 2004/043913, published on May 27, 2004 describes hetero substituted benzimidazole compounds and antiviral uses thereof.

International patent application WO/2004/085409, published on Oct. 7, 2004, discloses compound libraries showing kinase activity.

SUMMARY OF THE INVENTION

The invention answers the current need for selective and potent protein kinase inhibitors. One embodiment of the invention is directed to the novel compounds of Formula I:

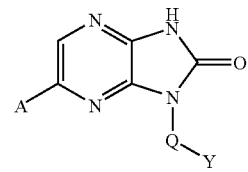

a stereoisomeric or tautomeric form thereof or a solvate, hydrate, or pharmaceutically acceptable salt thereof, wherein
Q is a direct link or $C_{2-12}$-alkenyl, $C_{1-12}$alkyl, $C_{1-12}$alkoxy, thio$C_{1-12}$alkyl, hydroxy$C_{1-12}$alkyl or carboxy$C_{1-12}$alkyl, amino$C_{1-12}$alkyl;
Y is selected from the group consisting of phenyl, naphthyl, indanyl and biphenyl, each of which may be optionally substituted with one, two, three or four substituents each independently selected from the group consisting of $C_{1-4}$alkyl, nitro, amino, amino$C_{1-12}$alkyl, halogen, hydroxy, —$CF_3$, $C_{1-12}$alkoxy, aryloxy, aryl$C_{1-12}$alkoxy, —CN, —$OCF_3$, —$COR_a$, —$COOR_a$, —$CONR_aR_b$, —$NR_aCOR_b$, —$SO_2R_a$, —$SO_3R_a$ or —$SO_2NR_aR_b$; wherein
each $R_a$ and $R_b$ are independently selected from the group consisting of hydrogen, $C_4$alkyl, $C_{3-6}$cycloalkyl, aryl, aryl$C_{1-6}$alkyl, heteroaryl or heteroaryl$C_{1-6}$alkyl;
two adjacent substituents may also be taken together to form a bivalent radical of formula selected from the group consisting of —O—$CH_2$—O—, —O—$CH_2$—$CH_2$—, —O—$CH_2$—$CH_2$—O—, —O—$CH_2$—$CH_2$—$CH_2$—; or
Y is a 5- to 7-membered monocyclic heteroaromatic ring having from one, two, three or four heteroatoms each independently selected from the group consisting of N, O and S, that monocyclic heteroatomic ring may be optionally substituted with one, two or three substituents independently selected from the group consisting of $C_{1-6}$ alkyl, amino, halogen, hydroxy, $C_{1-12}$alkoxy, aryloxy, aryl$C_{1-12}$alkoxy, —CN, —$CF_3$, —$OCF_3$, —$COR_c$, —$COOR_c$, —$CONR_cR_d$, —$NR_cCOR_d$, $NRCSO_2Rd$, —$SO_2RC$, —$SO_3R_c$ or —$SO_2NR_cR_d$,
wherein each $R_c$ and $R_d$ are independently selected from the group consisting of hydrogen, $C_{1-4}$alkyl, $C_{3-6}$ cycloalkyl, aryl, aryl$C_{1-6}$alkyl, heteroaryl or heteroaryl$C_{1-6}$alkyl; or
Y is a 8- to 10-membered bicyclic heteroaromatic ring having from one, two, three or four heteroatoms selected from the group consisting of N, O and S, that may bicyclic heteroaromatic ring may be optionally substituted with one, two or three substituents each independently selected from the group consisting of $C_{1-6}$-alkyl, amino, halogen, hydroxy, $C_{1-12}$alkoxy, aryloxy, aryl$C_{1-12}$alkoxy, —CN, —CF$_3$, —OCF$_3$, —COR$_e$, —COOR$_f$, —CONR$_e$R$_f$, —NR$_e$COR$_f$, NR$_e$SO$_2$R$_f$, —SO$_2$R$_e$, —SO$_3$R$_e$ or —SO$_2$NR$_e$R$_f$, wherein each R$_e$ and R$_f$ are independently hydrogen, $C_{1-4}$ alkyl, $C_{3-6}$ cycloalkyl, aryl, aryl$C_{1-6}$alkyl, heteroaryl or heteroaryl$C_{1-4}$alkyl;

A is phenyl, naphthyl or biphenyl, each of which may be optionally substituted with one or more substituents each independently selected from the group consisting of $C_{1-4}$alkyl, amino, amino$C_{1-12}$alkyl, halogen, hydroxy, hydroxy$C_{1-4}$alkyl, $C_{1-4}$alkyloxy$C_{1-4}$alkyl, —CF$_3$, $C_{1-12}$alkoxy, aryloxy, aryl$C_{1-2}$alkoxy, —CN, —OCF$_3$, —COR$_g$, —COOR$_g$, —CONR$_g$R$_h$, —NR$_g$COR$_h$, —SO$_2$R$_g$, —SO$_3$R$_g$ or —SO$_2$NR$_g$R$_h$, wherein each R$_g$ and R$_h$ are independently selected from the group consisting of hydrogen, $C_{1-4}$alkyl, $C_{3-6}$cycloalkyl, aryl, aryl$C_{1-6}$alkyl, heteroaryl or heteroaryl$C_{1-6}$alkyl; or A is a 5- to 6-membered monocyclic heteroaromatic ring having from one, two, three or four heteroatoms independently selected from the group consisting of N, O and S, that monocyclic heteroaromatic ring may be optionally substituted with one or more substituents each independently selected from the group consisting of $C_{1-6}$alkyl, amino, amino$C_{1-2}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —CF$_3$, —OCF$_3$, —COR$_i$, —COOR$_i$, —CONR$_i$R$_j$, —NR$_i$COR$_j$, —NR$_i$SO$_2$R$_j$, —SO$_2$R$_i$, —SO$_3$R$_i$ or —SO$_2$NR$_i$R$_j$, wherein each R$_i$ and R$_j$ are independently selected from the group consisting of hydrogen, $C_{1-4}$ alkyl, $C_{3-6}$cycloalkyl, aryl, aryl$C_1$-alkyl, heteroaryl or heteroaryl$C_{1-6}$alkyl; or A is a 8- to 10 membered bicyclic heteroaromatic ring from one, two, three or four heteroatoms selected from the group consisting of N, O and S, and may be optionally substituted with one, two or three substituents each independently selected from the group consisting of $C_{1-6}$alkyl, amino, amino$C_{1-12}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —CF$_3$, —OCF$_3$, —COR$_k$, —COOR$_k$, —CONR$_k$R$_l$, —NR$_k$COR$_l$, —NR$_k$SO$_2$R$_l$, —SO$_2$R$_k$, —SO$_3$R$_k$ or —SO$_2$NR$_k$R$_l$, wherein each R$_k$ and R$_l$ are independently selected from the group consisting of hydrogen, $C_{1-4}$ alkyl, $C_{3-6}$ cycloalkyl, aryl, aryl$C_{1-6}$alkyl, heteroaryl or heteroaryl$C_{1-6}$alkyl.

The compounds of Formula (I) are especially potent inhibitors of the kinases, more in particular the Aurora family of protein kinases. Hence the present invention relates also to the use of the compounds of formula (I) as kinase activity modulators, more specifically Aurora activity modulators, especially the use as Aurora inhibitors.

The invention also relates to methods of inhibiting protein tyrosine kinase activity in a mammal by administration of a therapeutically effective amount of at least one compound of Formula (I).

The invention also relates to pharmaceutical compositions comprising the compounds of Formula (I).

The invention further relates to the use of compounds of formula (I) as a medicine and also to the use of the compounds of formula (I) for the manufacture of a medicament for treating kinase activity-related conditions and disease, more in particular a medicament for treating Aurora activity-related conditions and diseases, especially cancers.

The invention further relates to the use of compounds of formula (I) as a tool for assessing protein kinase activity, more in particular the use of compounds of formula (I) for assessing Aurora 1, Aurora 2 and/or Aurora 3 activity.

DETAILED DESCRIPTION OF THE INVENTION

The invention is directed to the novel compounds of Formula I:

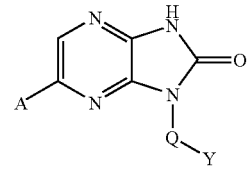

a stereoisomeric or tautomeric form thereof or a solvate, hydrate, or pharmaceutically acceptable salt thereof, wherein
Q is a direct link or $C_{2-12}$-alkenyl, $C_{1-12}$alkyl, $C_{1-12}$alkoxy, thio$C_{1-12}$alkyl, hydroxy$C_{1-12}$alkyl or carboxy$C_{1-12}$alkyl, amino$C_{1-12}$alkyl;
Y is selected from the group consisting of phenyl, naphthyl, indanyl and biphenyl, each of which may be optionally substituted with one, two, three or four substituents each independently selected from the group consisting of $C_{1-4}$alkyl, nitro, amino, amino$C_{1-12}$alkyl, halogen, hydroxy, —CF$_3$, $C_{1-12}$alkoxy, aryloxy, aryl$C_{1-12}$alkoxy, —CN, —OCF$_3$, —COR$_a$, —COOR$_a$, —CONR$_a$R$_b$, —NR$_a$COR$_b$, —SO$_2$R$_a$, —SO$_3$R$_a$ or —SO$_2$NR$_a$R$_b$; wherein
each R$_a$ and R$_b$ are independently selected from the group consisting of hydrogen, $C_{1-4}$alkyl, $C_{3-6}$cycloalkyl, aryl, aryl$C_{1-6}$alkyl, heteroaryl or heteroaryl$C_{1-6}$alkyl; two adjacent substituents may also be taken together to form a bivalent radical of formula selected from the group consisting of —O—CH$_2$—O—, —O—CH$_2$—CH$_2$—, —O—CH$_2$—CH$_2$—O—, —O—CH$_2$—CH$_2$—CH$_2$—; or
Y is a 5- to 7-membered monocyclic heteroaromatic ring having from one, two, three or four heteroatoms each independently selected from the group consisting of N, O and S, that monocyclic heteroatomic ring may be optionally substituted with one, two or three substituents independently selected from the group consisting of $C_{1-6}$ alkyl, amino, halogen, hydroxy, $C_{1-12}$alkoxy, aryloxy, aryl$C_{1-12}$alkoxy, —CN, —CF$_3$, —OCF$_3$, —COR$_c$, —COOR$_c$, —CONR$_c$R$_d$, —NR$_c$COR$_d$, NR$_c$SO$_2$R$_d$, —SO$_2$R$_c$, —SO$_3$R$_c$ or —SO$_2$NR$_c$R$_d$,
wherein each R$_c$ and R$_d$ are independently selected from the group consisting of hydrogen, $C_{1-4}$alkyl, $C_{3-6}$ cycloalkyl, aryl, aryl$C_{1-6}$alkyl, heteroaryl or heteroaryl$C_{1-6}$alkyl; or
Y is a 8- to 10-membered bicyclic heteroaromatic ring having from one, two, three or four heteroatoms selected from the group consisting of N, O and S, that may bicyclic heteroaromatic ring may be optionally substituted with one, two or three substituents each independently selected from the group consisting of $C_{1-6}$-alkyl, amino, halogen, hydroxy, $C_{1-12}$alkoxy, aryloxy, aryl$C_{1-12}$alkoxy, —CN, —CF$_3$, —OCF$_3$, —COR$_e$, —COOR$_f$, —CONR$_e$R$_f$, —NR$_e$COR$_f$, NR$_e$SO$_2$R$_f$, —SO$_2$R$_e$, —SO$_3$R$_e$ or —SO$_2$NR$_e$R$_f$, wherein each R$_e$ and R$_f$ are independently hydrogen, $C_{1-4}$ alkyl, $C_{3-6}$ cycloalkyl, aryl, aryl$C_{1-6}$alkyl, heteroaryl or heteroaryl$C_{1-4}$alkyl;
A is phenyl, naphthyl or biphenyl, each of which may be optionally substituted with one or more substituents each independently selected from the group consisting of $C_{1-4}$alkyl, amino, amino$C_{1-12}$alkyl, halogen, hydroxy, hydroxy$C_{1-4}$alkyl, $C_{1-4}$alkyloxy$C_{1-4}$alkyl, —CF$_3$, $C_{1-12}$alkoxy, aryloxy, aryl$C_{1-12}$alkoxy, —CN, —OCF$_3$, —COR$_g$, —COOR$_g$, —CONR$_g$R$_h$, —NR$_g$COR$_h$, —SO$_2$R$_g$, —SO$_3$R$_g$ or —SO$_2$NR$_g$R$_h$, wherein each R$_g$ and R$_h$ are independently selected from the group consisting of hydrogen, C$_{1-4}$alkyl, C$_{3-6}$cycloalkyl, aryl, arylC$_{1-6}$alkyl, heteroaryl or heteroarylC$_{1-6}$alkyl; or A is a 5- to 6-membered monocyclic heteroaromatic ring having from one, two, three or four heteroatoms independently selected from the group consisting of N, O and S, that monocyclic heteroaromatic ring may be optionally substituted with one or more substituents each independently selected from the group consisting of C$_{1-6}$alkyl, amino, aminoC$_{1-12}$alkyl, halogen, hydroxy, hydroxyC$_{1-4}$alkyl, C$_{1-4}$alkyloxyC$_{1-4}$alkyl, C$_{1-12}$alkoxy, aryloxy, aryl C$_{1-12}$alkoxy, —CN, —CF$_3$, —OCF$_3$, —COR$_i$, —COOR$_i$, —CONR$_i$R$_j$, —NR$_i$COR$_j$, —NR$_i$SO$_2$R$_j$, —SO$_2$R$_i$, —SO$_3$R$_i$ or —SO$_2$NR$_i$R$_j$, wherein each R$_i$ and R$_j$ are independently selected from the group consisting of hydrogen, C$_{1-4}$ alkyl, C$_{3-6}$cycloalkyl, aryl, arylC$_{1-6}$alkyl, heteroaryl or heteroarylC$_{1-6}$alkyl; or A is a 8- to 10 membered bicyclic heteroaromatic ring from one, two, three or four heteroatoms selected from the group consisting of N, O and S, and may be optionally substituted with one, two or three substituents each independently selected from the group consisting of C$_{1-6}$alkyl, amino, aminoC$_{1-12}$alkyl, halogen, hydroxy, hydroxyC$_{1-4}$alkyl, C$_{1-4}$alkyloxyC$_{1-4}$alkyl, C$_{1-12}$alkoxy, aryloxy, aryl C$_{1-12}$alkoxy, —CN, —CF$_3$, —OCF$_3$, —COR$_k$, —COOR$_k$, —CONR$_k$R$_l$, —NR$_k$COR$_l$, —NR$_k$SO$_2$R$_l$, —SO$_2$R$_k$, —SO$_3$R$_k$ or —SO$_2$NR$_k$R$_l$, wherein each R$_k$ and R$_l$ are independently selected from the group consisting of hydrogen, C$_{1-4}$ alkyl, C$_{3-6}$ cycloalkyl, aryl, arylC$_{1-6}$alkyl, heteroaryl or heteroarylC$_{1-6}$alkyl.

Interesting compounds are those compounds the compounds wherein one of the following restrictions apply:

1) Q is C$_{2-12}$alkenyl or C$_{2-12}$alkyl, especially C$_{1-6}$alkyl, more particularly C$_{1-4}$alkyl, preferably ethylene or methylene;

2) Y is phenyl, naphthyl, biphenyl or indanyl, each of which may be optionally substituted with one, two or three substituents selected from the group consisting of C$_{1-6}$alkyl; nitro, amino, halogen, hydroxyC$_{1-6}$alkyl, hydroxy, —CF$_3$ or C$_{1-6}$alkyloxy; or the two substituents on Y are taken together to form a bivalent radical of formula —O—CH$_2$—O—, or Y is a 5 or 6 membered heteroaromatic ring having one hetereoatom selected from the group consisting of N and S; preferably Y is a optionally substituted phenyl;

3) A is a phenyl, naphthyl or biphenyl, each of which may be optionally substituted with one or more of C$_{1-6}$alkyl, halogen, hydroxy, —CF$_3$, C$_{1-6}$alkyloxy, —CN, —OCF$_3$; a 5- to 6-membered monocyclic heteroaromatic ring having from one to four heteroatoms selected from N, O or S, that may be optionally substituted with C$_{1-6}$ alkyl, halogen, hydroxyC$_{1-6}$alkyl, hydroxy, C$_{1-6}$alkyloxy; more in particular isoxazolyl; or a a 8- to 10 membered bicyclic heteroaromatic ring having from one to four heteroatoms selected from N, O or S, and may be optionally substituted with C$_{1-6}$alkyl, halogen, hydroxyC$_{1-6}$alkyl, hydroxy, C$_{1-6}$alkyloxy.

More interesting compounds are those compounds of Formula (I) wherein Q is methylene or ethylene; wherein Y is phenyl optionally substituted with halogen, cyano or methoxy; wherein A is either phenyl optionally substituted with up to three substituents selected from the group consisting of C$_{1-6}$alkyl, halogen, hydroxyC$_{1-6}$alkyl, hydroxy, C$_{1-6}$alkyloxy; or a 5 membered monocyclic heteroaromatic ring having a N and a O atom in the ring, optionally substituted with up to three substituents selected from the group consisting of C$_{1-6}$alkyl, halogen, hydroxyC$_{1-6}$alkyl, hydroxy, C$_{1-6}$alkyloxy; or a 9 membered bicyclic heteroaromatic ring having a N-atom in one of the rings, optionally substituted with with up to three substituents selected from the group consisting of C$_{1-6}$alkyl, halogen, hydroxyC$_{1-6}$alkyl, hydroxy, C$_{1-6}$alkyloxy.

Preferred compounds are the compounds of Formula (I) wherein Q is methylene or ethylene; wherein Y is phenyl, indanyl, thienyl or pyridine; wherein A is phenyl optionally substituted with up to three substituents each independently-selected from the group consisting of methyl, chloro, fluoro, hydroxymethyl, hydroxy, amino, methoxy, carboxy.

Particularly preferred compounds of Formula (I) include, but are not limited to, 1-((S)-(–)-1-Phenyl-ethyl)-6-(3,4,5-trimethoxy-phenyl)-1,3-dihydro-imidazo[4,5-b]pyrazin-2-one, 1-((R)-(+)-1-Phenyl-ethyl)-6-(3,4,5-trimethoxy-phenyl)-1,3-dihydro-imidazo[4,5-b]pyrazin-2-one, 1-Benzyl-6-(3,4,5-tri methoxy-phenyl)-1,3-dihydro-imidazo[4,5-b]pyrazin-2-one, 6-(1H-Indol-5-yl)-1-((S)-(–)-1-phenyl-ethyl)-1,3-dihydro-imidazo[4,5-b]pyrazin-2-one, 6-(3,5-Dimethyl-isoxazol-4-yl)-1-((S)-(–)-1-phenyl-ethyl)-1,3-dihydro-imidazo[4,5-b]pyrazin-2-one, 3-[2-Oxo-3-((S)-(–)-1-phenyl-ethyl)-2,3-dihydro-1H-imidazo[4,5-b]pyrazin-5-yl]-benzonitrile, 6-(3-Hydroxymethyl-phenyl)-1-((S)-(–)-1-phenyl-ethyl)-1,3-dihydro-imidazo[4,5-b]pyrazin-2-one, 6-(1H-Indol-2-yl)-1-((S)-(–)-1-phenyl-ethyl)-1,3-dihydro-imidazo[4,5-b]pyrazin-2-one, 1-Benzyl-6-pyridin-3-yl-1,3-dihydroimidazo[4,5-b]pyrazin-2-one, 1-Benzyl-6-(3,4-dimethoxyphenyl)-1,3-dihydroimidazo[4,5-b]pyrazin-2-one, 1-Benzyl-6-(6-methoxypyridin-3-yl)-1,3-dihydroimidazo[4,5-b]pyrazin-2-one, 1-Benzyl-6-(3-methoxymethylphenyl)-1,3-dihydroimidazo[4,5-b]pyrazin-2-one, 6-(3-Acetylphenyl)-1-benzyl-1,3-dihydroimidazo[4,5-b]pyrazin-2-one, 1-Benzyl-6-(2,4-dimethoxyphenyl)-1,3-dihydroimidazo[4,5-b]pyrazin-2-one, 1-Benzyl-6-thiophen-3-yl-1,3-dihydroimidazo[4,5-b]pyrazin-2-one, 1-Benzyl-6-thiophen-2-yl-1,3-dihydro-imidazo[4,5-b]pyrazin-2-one, 1-Benzyl-6-(3-methoxyphenyl)-1,3-dihydroimidazo[4,5-b]pyrazin-2-one, 3-(3-Benzyl-2-oxo-2,3-dihydro-1H-imidazo[4,5-b]pyrazin-5-yl)-benzoic acid, 1-Pyridin-2-ylmethyl-6-(3,4,5-trimethoxyphenyl)-1,3-dihydroimidazo-[4,5-b]pyrazin-2-one, 1-Pyridin-3-ylmethyl-6-(3,4,5-trimethoxyphenyl)-1,3-dihydro-imidazo[4,5-b]pyrazin-2-one, 1-Benzyl-6-(3,5-dimethoxyphenyl)-1,3-dihydro-imidazo[4,5-b]pyrazin-2-one, 5-(3-Benzyl-2-oxo-2,3-dihydro-1H-imidazo[4,5-b]pyrazin-5-yl)-2-methoxybenzaldehyde, 5-(3-Benzyl-2-oxo-2,3-dihydro-1H-imidazo[4,5-b]pyrazin-5-yl)-2-methoxybenzoic acid, 1-Benzyl-6-(3-hydroxymethyl-4-methoxyphenyl)-1,3-dihydroimidazo[4,5-b]pyrazin-2-one, 5-(3-Benzyl-2-oxo-2,3-dihydro-1H-imidazo[4,5-b]pyrazin-5-yl)-2-hydroxybenzoic acid, 5-(3-Benzyl-2-oxo-2,3-dihydro-1H-imidazo[4,5-b]pyrazin-5-yl)-2-methoxybenzamide, 1-(3-Nitrobenzyl)-6-(3,4,5-trimethoxyphenyl)-1,3-dihydroimidazo[4,5-b]pyrazin-2-one, 1-(4-Chlorobenzyl)-6-(3,4,5-trimethoxyphenyl)-1,3-dihydroimidazo[4,5-b]pyrazin-2-one, 1-(3-Chlorobenzyl)-6-(3,4,5-trimethoxyphenyl)-1,3-dihydroimidazo[4,5-b]pyrazin-2-one, 1-(3-Methylbenzyl)-6-(3,4,5-trimethoxyphenyl)-1,3-dihydroimidazo[4,5-b]pyrazin-2-one, 1-(3-Fluorobenzyl)-6-(3,4,5-tri methoxyphenyl)-1,3-dihydroimidazo[4,5-b]pyrazin-2-one, 1-(3-Methoxybenzyl)-6-(3,4,5-trimethoxyphenyl)-1,3-dihydroimidazo[4,5-b]pyrazin-2-one, 1-Naphthalen-1-ylmethyl-6-(3,4,5-trimethoxyphenyl)-1,3-dihydroimidazo[4,5-b]pyrazin-2-one, 1-Benzo[1,3]dioxol-5-ylmethyl-6-(3,4,5-trimethoxyphenyl)-1,3-dihydroimidazo[4,5-b]pyrazin-2- one, 1-Indan-1-yl-6-(3,4,5-trimethoxyphenyl)-1,3-dihydroimidazo[4,5-b]pyrazin-2-one, 1-Thiophen-2-ylmethyl-6-(3,4,5-trimethoxyphenyl)-1,3-dihydroimidazo[4,5-b]pyrazin-2-one, 1-(2-Chlorobenzyl)-6-(3,4,5-trimethoxyphenyl)-1,3-dihydroimidazo[4,5-b]pyrazin-2-one, 1-(4-Aminobenzyl)-6-(3,4,5-trimethoxyphenyl)-1,3-dihydroimidazo[4,5-b]pyrazin-2-one, 1-(3-Aminobenzyl)-6-(3,4,5-trimethoxyphenyl)-1,3-dihydroimidazo[4,5-b]pyrazin-2-one, the solvates, hydrates and pharmaceutically acceptable salts thereof.

Particularly Preferred Compounds are:
6-(1H-Indol-5-yl)-1-((S)-(−)-1-phenyl-ethyl)-1,3-dihydro-imidazo[4,5-b]pyrazin-2-one, 6-(3,5-Dimethyl-isoxazol-4-yl)-1-((S)-(−)-1-phenyl-ethyl)-1,3-dihydro-imidazo[4,5-b]pyrazin-2-one, 3-[2-Oxo-3-((S)-(−)-1-phenyl-ethyl)-2,3-dihydro-1H-imidazo[4,5-b]pyrazin-5-yl]-benzonitrile, 6-(1H-Indol-2-yl)-1-((S)-(−)-1-phenyl-ethyl)-1,3-dihydro-imidazo[4,5-b]pyrazin-2-one, 1-Benzyl-6-(3,4-dimethoxyphenyl)-1,3-dihydroimidazo[4,5-b]pyrazin-2-one, 1-Benzyl-6-(6-methoxypyridin-3-yl)-1,3-dihydroimidazo[4,5-b]pyrazin-2-one, 1-Benzyl-6-(3-methoxymethylphenyl)-1,3-dihydroimidazo[4,5-b]pyrazin-2-one, 6-(3-Acetylphenyl)-1-benzyl-1,3-dihydroimidazo[4,5-b]pyrazin-2-one, 1-Benzyl-6-(2,4-dimethoxyphenyl)-1,3-dihydroimidazo[4,5-b]pyrazin-2-one, 1-Benzyl-6-thiophen-2-yl-1,3-dihydro-imidazo[4,5-b]pyrazin-2-one, 3-(3-Benzyl-2-oxo-2,3-dihydro-1H-imidazo[4,5-b]pyrazin-5-yl)-benzoic acid, 1-Benzyl-6-(3,5-dimethoxyphenyl)-1,3-dihydro-imidazo[4,5-b]pyrazin-2-one, 5-(3-Benzyl-2-oxo-2,3-dihydro-1H-imidazo[4,5-b]pyrazin-5-yl)-2-methoxybenzaldehyde, 5-(3-Benzyl-2-oxo-2,3-dihydro-1H-imidazo[4,5-b]pyrazin-5-yl)-2-methoxybenzoic acid, 1-Benzyl-6-(3-hydroxymethyl-4-methoxyphenyl)-1,3-dihydroimidazo[4,5-b]pyrazin-2-one, 5-(3-Benzyl-2-oxo-2,3-dihydro-1H-imidazo[4,5-b]pyrazin-5-yl)-2-hydroxybenzoic acid, 5-(3-Benzyl-2-oxo-2,3-dihydro-1H-imidazo[4,5-b]pyrazin-5-yl)-2-methoxybenzamide, 1-(3-Nitrobenzyl)-6-(3,4,5-trimethoxyphenyl)-1,3-dihydroimidazo[4,5-b]pyrazin-2-one, 1-(3-Chlorobenzyl)-6-(3,4,5-trimethoxyphenyl)-1,3-dihydroimidazo[4,5-b]pyrazin-2-one, 1-(3-Methylbenzyl)-6-(3,4,5-trimethoxyphenyl)-1,3-dihydroimidazo[4,5-b]pyrazin-2-one, 1-(3-Fluorobenzyl)-6-(3,4,5-trimethoxyphenyl)-1,3-dihydroimidazo[4,5-b]pyrazin-2-one, 1-(3-Methoxybenzyl)-6-(3,4,5-trimethoxyphenyl)-1,3-dihydroimidazo[4,5-b]pyrazin-2-one, 1-Naphthalen-1-ylmethyl-6-(3,4,5-trimethoxyphenyl)-1,3-dihydroimidazo[4,5-b]pyrazin-2-one, 1-Benzo[1,3]dioxol-5-ylmethyl-6-(3,4,5-trimethoxyphenyl)-1,3-dihydroimidazo[4,5-b]pyrazin-2-one, 1-Indan-1-yl-6-(3,4,5-trimethoxyphenyl)-1,3-dihydroimidazo[4,5-b]pyrazin-2-one, 1-(2-Chlorobenzyl)-6-(3,4,5-trimethoxyphenyl)-1,3-dihydroimidazo[4,5-b]pyrazin-2-one, 1-(4-Aminobenzyl)-6-(3,4,5-trimethoxyphenyl)-1,3-dihydroimidazo[4,5-b]pyrazin-2-one, 1-(3-Aminobenzyl)-6-(3,4,5-trimethoxyphenyl)-1,3-dihydroimidazo[4,5-b]pyrazin-2-one; the solvates, hydrates and pharmaceutically acceptable salts thereof.

The invention also relates to methods of inhibiting protein kinase activity in a mammal by administration of a therapeutically effective amount of at least one compound of formula (I).

The invention is considered to include the enantiomeric, diastereomeric and tautomeric forms of all compounds of formula (I). These enantiomeric, diastereomeric and tautomeric forms can be in a pure form or a substantialy pure form as well as in mixtures such as racemic mixtures or other mixtures thereof.

The invention is considered to include the solvates, hydrates and the like of the compounds of formula (I). When the term "compounds of formula (I)" is used, it can be meant to includes the enantiomeric, diastereomeric, tautomeric forms that would corresponds to the structure. It can be meant to include mixtures of such enantiomers and diastereomers and tautomers. It can further be meant to include the solvates and hydrates of the compounds of formula (I).

I. Definitions

The term "$C_{1-12}$alkyl", whether used alone or as part of a substituent group, refers to both linear and branched chain radicals of up to 12 carbon atoms, unless otherwise indicated, and includes, but is not limited to methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl and the like.

The term "$C_{1-6}$alkyl", whether used alone or as part of a substituent group, specifically includes the radicals methyl, ethyl, propyl, butyl, pentyl, hexyl and the like.

The term "$C_{1-4}$alkyl", whether used alone or as part of a substituent group, specifically includes the radicals methyl, ethyl, propyl and butyl.

The term "heterocyclyl" refers to a nonaromatic ring composed of from 3 to 7 carbon atoms and at least one heteroatom selected from N, O or S. Alkyl substituents may optionally be present on the ring. Examples include tetrahydrofuryl, dihydropyranyl, 2,5-dimethypiperidyl, morpholinyl and piperazinyl.

The term "heterocyclyl$C_{1-6}$alkyl" refers to a $C_{1-6}$alkyl group linked a heterocyclyl substituent. Examples include dihydropyranylethyl and 2-morpholinylpropyl.

The term "$C_{2-12}$alkenyl", whether used alone or as part of a substituent group, refers to an alkenyl or alkendiyl radical containing up to 12 carbon atoms with at least one carbon to carbon double bond. Typically, one carbon-carbon double bond is present; the radical may be in either the cis or trans conformation about the double bond(s). Examples include ethenyl, propenyl, butenyl, pentenyl, hexenyl, heptenyl, octenyl, nonenyl, and the like.

The term "hydroxyalkyl" refers to at least one hydroxyl group bonded to any carbon atom along an alkyl chain. Alkyl may be specified as $C_{1-12}$ alkyl for example whereby then $C_{1-12}$alkyl would have the definition as shown above. The term "hydroxy$C_{1-12}$alkyl" refers to a $C_{1-12}$alkyl as defined above with one hydroxy group bonded to any carbon atom along the alkyl chain.

The term "aminoalkyl" refers to at least one primary or secondary amino group bonded to any carbon atom along an alkyl chain. Alkyl may be specified as $C_{1-12}$ alkyl for example whereby then $C_{1-12}$ alkyl would have the definition as given. The term amino$C_{1-12}$alkyl refers to $C_{1-12}$alkyl as defined above with one an amino group bonded to any carbon atom along an alkyl chain.

The term "thioalkyl" refers to at least one sulfur group bonded to any carbon atom along an alkyl chain. The sulfur group may be at any oxidation state and includes sulfoxides, sulfones and sulfates. Alkyl may be specified as $C_{1-12}$ alkyl for example whereby then $C_{1-12}$ alkyl would have the definition as given. The term "thio$C_{1-12}$alkyl" refers to $C_{1-12}$alkyl as defined above with one sulfur group bonded to any carbon atom along an alkyl chain.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters. Alkyl may be specified as $C_{1-12}$alkyl for example whereby then $C_{1-2}$alkyl would have the definition as given. The term "carboxy$C_{1-12}$alkyl" refers to $C_{1-12}$alkyl as defined above with one carboxy group bonded to any carbon atom along an alkyl chain.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl, thienyl, indolyl, isoindolyl, benzofuranyl, indazolyl, purinyl, quinolizinyl, indolizinyl, cinnolinyl, phthalazinyl, quinazolinyl, pyrrolyl and the like.

The term "aryloxy" refers to an aryl group bonded to an oxygen atom, which in turn is linked to the rest of the molecule.

The term "heteroaryl$C_{1-6}$alkyl" refers to a $C_{1-6}$alkyl group linked to a heteroaryl substituent. Examples include furylethyl and 2-quinolinylpropyl.

The term "heteroatom" refers to a nitrogen atom, an oxygen atom or a sulfur atom wherein the nitrogen and sulfur atoms can exist in any allowed oxidation states.

The term "$C_{1-12}$alkyloxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring and optionally substituted with 1-3 substituents selected from alkoxy, alkyl, halogen, hydroxy and heteroaryl. Examples include benzene, biphenyl and napthalene.

The term "aryl$C_{1-6}$alkyl" refers to a $C_{1-6}$alkyl group linked to an aryl substituent. Examples include benzyl, phenylethyl or 2-naphthylmethyl.

The term "acyl" refers to the group —C(O)$R_x$, where $R_x$ is $C_{1-12}$alkyl, aryl, aryl$C_{1-6}$alkyl, heteroaryl and heteroaryl$C_{1-6}$alkyl. An "acylating agent" adds the —C(O)$R_x$ group to a molecule.

The term "sulfonyl" refers to the group —S(O)$_2$$R_y$, where $R_y$ is $C_{1-12}$alkyl, aryl, aryl$C_{1-6}$alkyl, heteroaryl and heteroaryl$C_{1-6}$alkyl. A "sulfonylating agent" adds the —S(O)$_2$$R_y$ group to a molecule.

The term "$C_{3-6}$cycloalkyl", whether used alone or as part of a substituent group, refers to a saturated monocyclic alkyl ring system radical. Examples of cycloalkyl ring systems include, but are not limited to, cyclopropyl, cyclobutyl, cyclopentyl, cyclohexyl and the like.

The present invention contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superposable. The term "diastereomer" refers to stereoisomers that are not related as mirror images. The symbols "R" and "S" represent the configuration of substituents around a chiral carbon atom(s). The symbols "R*" and "S*" denote the relative configurations of of substituents around a chiral carbon atom(s).

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) or "chair" configuration, the substituents are on opposite sides in relationship to the carbon-carbon double bond; in the "Z" (same sided) or "boat" configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "S*," "R*," "E," "Z," "cis," "trans," "exo" and "endo" are used as described herein for indicating atom configuration(s) relative to a core molecule and are intended to be used as defined in the literature (IUPAC Recommendations for Fundamental Stereochemistry (Section E), Pure Appl. Chem., 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

The term "tautomer" refers to "tautomerism" that designates a rapid and reversible interconversion of isomers associated with the actual movement of electrons as well as one or more hydrogen atoms. Each tautomeric structure is capable of independent existence and potential isolation. An art-known example of tautomerism is keto-enol tautomerism.

Furthermore, the compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

II. Therapeutic Uses

The compounds of Formula I represent novel potent inhibitors of protein kinases and may be useful in the prevention and treatment of disorders resulting from actions of these kinases.

The invention also provides methods of inhibiting a protein kinase comprising contacting the protein kinase with an effective inhibitory amount of at least one of the compounds of Formula I. The protein kinases, which may be inhibited, include, but are not limited to, Aurora-1, Aurora-2 and Aurora-3 kinases.

In various embodiments of the invention, the protein kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, breast cancer, colon cancer, stomach cancer, lung cancer, leukemia and lymphoma. In one embodiment of the invention, an effective amount of at least one compound of Formula I is administered in combination with an effective amount of a chemotherapeutic agent.

The foregoing methods contemplate that the compounds of the present invention are therapeutically useful for treating, preventing or ameliorating diseases disorders or conditions such as, without limitation, osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus), heart disease (such as atherosclerosis, neointima formation or transplantation-induced vasculopathies (such as restenosis and the like), lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like).

The term "administering," with respect to the methods of the present invention, refers to a means for treating, ameliorating or preventing a disease, disorder or syndrome as described herein with a compound specifically disclosed or a compound or prodrug thereof, which would obviously be included within the scope of the invention albeit not specifically disclosed for certain of the instant compounds.

Such methods include therapeutically administering an effective amount of one or more compounds of Formula (I) or a composition or medicament thereof at different times during the course of a therapy or concurrently in a combination form. Such methods further include therapeutically administering an effective amount of one or more compounds of Formula (I) with one or more therapeutic agents at different times during the course of a therapy or concurrently in a combination form.

The term "subject" as used herein, refers to an animal, preferably a mammal, most preferably a human, who has been the object of treatment, observation or experiment and is at risk of (or susceptible to) developing a disease or disorder or having a disease or disorder related to unregulated kinase activity. The term "effective amount" refers to that amount of active compound or pharmaceutical agent that elicits the biological or medicinal response (such as inhibiting activation of unregulated kinase activity) in a tissue system, animal or human, that is being sought by a researcher, veterinarian, medical doctor, or other clinician, which includes alleviation of the symptoms of the disease or disorder being treated.

The term "combination therapy" refers to the use of one or more compounds of Formula (I) or composition or medicament thereof in combination with one or more therapeutic agents for the treatment of a number of different kinase mediated disorders and advantageously may facilitate the use of a reduced effective dose of the compound of Formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The terms "treating" or "preventing" refer, without limitation, to facilitating the eradication of, inhibiting the progression of or promoting stasis of a malignancy. The term "radiation therapy" refers to a therapy that comprises exposing the subject in need thereof to radiation. The present invention includes a method for administering one or more compounds of Formula (I) or composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

When employed as protein kinase inhibitors, the compounds of the invention may be administered in an effective amount within the dosage range of about 0.5 mg to about 10 g, preferably between about 0.5 mg to about 5 g in single or divided daily doses. The dosage administered will be affected by factors such as the route of administration, the health, weight and age of the recipient, the frequency of the treatment and the presence of concurrent and unrelated treatments.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The term "composition" refers to a product containing a compound of the present invention (such as a product comprising the specified ingredients in the specified amounts, as well as any product which results, directly or indirectly, from such combinations of the specified ingredients in the specified amounts).

The term "medicament" refers to a product for use in treating or ameliorating a kinase mediated disorder or condition.

The pharmaceutically acceptable salts of the compounds of Formula I include the conventional non-toxic salts or the quaternary ammonium salts, which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

III. Methods of Preparation

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. Except where indicated, starting materials and intermediates used in the schemes and examples are prepared by known methodologies well within the ordinary skill of persons versed in the art. No attempt has been made to optimize the yields obtained in any of the example reactions. One skilled in the art would also know how to increase such yields through routine variations in materials, solvents, reagents, reaction conditions and the like. All commercially available chemicals were obtained from commercial suppliers and used without further purification. Particular equipment components used in the examples such as reaction vessels and the like are also commercially available.

The terms used in describing the invention are commonly used and known to those skilled in the art. When used herein, the following abbreviations have the indicated meanings:
BuOH: Butanol
t-BuOH: tertiary butanol
DCM: Dichloromethane
DMSO: Dimethylsulfoxide
EtOAc: Ethyl Acetate
EtOH: Ethanol
MeOH: Methanol
NMR: Nuclear Magnetic Resonance
$Pr_2NEt$: Diisopropylethylamine
rt: room temperature
THF: Tetrahydrofuran

EXAMPLE 1

1-((S)-(−)-1-Phenylethyl)-6-(3,4,5-trimethoxyphenyl)-1,3-dihydroimidazo[4,5-b]pyrazin-2-one (Compound 1)

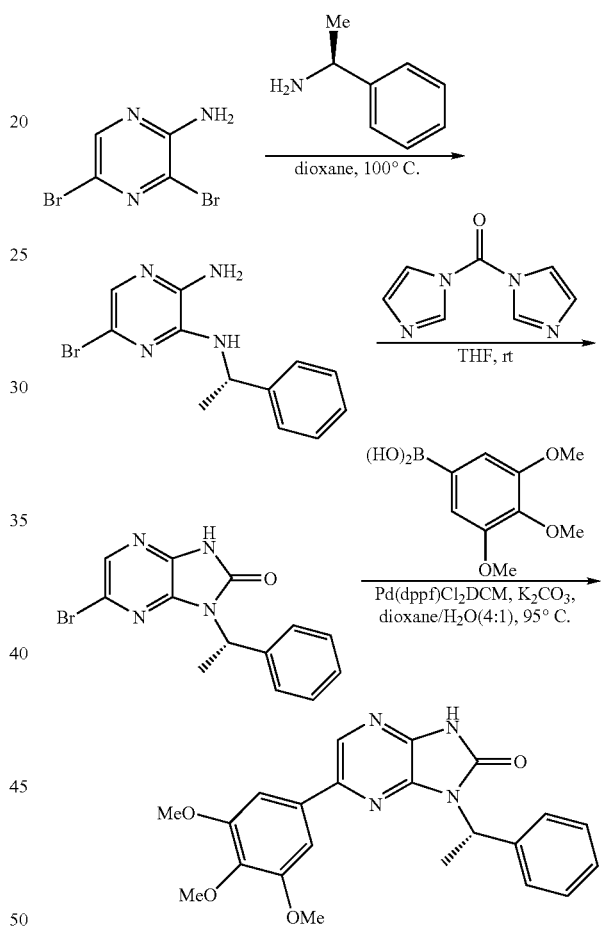

To a solution of 3,5-dibromopyrazin-2-ylamine (1.0 g; 3.95 mmol) in anhydrous dioxane (10 mL) was added (S)-(−)-1-phenylethylamine (0.51 mL; 3.95 mmol) at room temperature. The solution was heated to 100° C. and stirred for 20 h. After concentration under reduced pressure, the resultant residue was purified by flash chromatography [silica gel, hexanes/ethyl acetate (2:1)] to afford 5-bromo-$N^3$-(1-phenylethyl)pyrazine-2,3-diamine as a brown solid (0.69 g; 60%). $^1$H NMR (300 MHz, DMSO): δ 7.37-7.29 (m, 5H), 7.14 (s, 1H), 6.84 (d, J=7.2 Hz, 1H), 6.29 (s, 2H), 5.10-5.05 (m, 1H), 1.47 (d, J=6.9 Hz, 3H).

To a solution of 5-bromo-$N^3$-(1-phenylethyl)pyrazine-2,3-diamine (1.77 g, 6.04 mmol) in anhydrous tetrahydrofuran (30 mL) was added diimidazol-1-ylmethanone (1.47 g, 9.06 mmol) at room temperature. After stirring for 20 h, the reaction was concentrated under reduced pressure. Purification of the resultant residue by flash chromatography [silica gel; hexanes/ethyl acetate (2:1)] afforded 6-bromo-1-(1-phenylethyl)-1,3-dihydroimidazo[4,5-b]pyrazin-2-one as a red brown solid (1.64 g, 85%). $^1$H NMR (300 MHz, DMSO): δ 12.31 (s, 1H), 8.04 (s, 1H), 7.40-7.27 (m, 5H), 5.61 (q, J=7.2 Hz, 1H), 1.90 (d, J=7.2 Hz, 3H).

To a solution of 6-bromo-1-(1-phenylethyl)-1,3-dihydroimidazo[4,5-b]pyrazin-2-one (47.2 mg, 0.15 mmol), 3,4,5-trimethoxyphenyl boronic acid (31.8 mg, 0.15 mmol) and potassium carbonate (62.2 mg, 0.45 mmol) in degassed 20% aq. dioxane (5 mL) was added dichloro[1,1'-bis(diphenylphosphino)ferrocene]palladium (II) dichloromethane adduct (12 mg, 0.015 mmol) under an argon atmosphere. The mixture was stirred at 95° C. for 20 h, then cooled to room temperature and concentrated under reduced pressure. Purification of the resultant residue by flash chromatography [hexanes/ethyl acetate (2:1)] afforded 1-(1-phenylethyl)-6-(3,4,5-trimethoxyphenyl)-1,3-dihydro-imidazo[4,5-b]pyrazin-2-one as a white solid (36.6 mg, 60%). $^1$H NMR (300 MHz, DMSO): δ 12.10 (s, 1H), 8.53 (s, 1H), 7.51 (d, J=5.7 Hz, 2H), 7.33 (dd, J=5.7, 6.0 Hz, 2H), 7.26-7.22 (m, 1H), 7.23 (s, 2H), 5.71 (q, J=5.1 Hz, 1H), 3.84 (s, 6H), 3.67 (s, 3H), 1.97 (d, J=5.1 Hz, 3H). MS: 407.4 (M+H).

EXAMPLE 2

1-((R)-(+)-1-Phenylethyl)-6-(3,4,5-trimethoxyphenyl)-1,3-dihydro-imidazo[4,5-b]pyrazin-2-one (Compound 2)

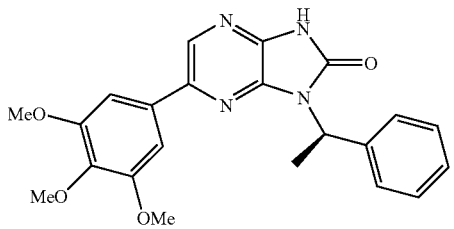

Prepared according to the procedure described for Example 1, in 30% overall yield. $^1$H NMR (300 MHz, DMSO): δ 12.10 (s, 1H), 8.53 (s, 1H), 7.51 (d, J=5.7 Hz, 2H), 7.33 (dd, J=5.7, 6.0 Hz, 2H), 7.26-7.22 (m, 1H), 7.23 (s, 2H), 5.71 (q, J=5.1 Hz, 1H), 3.84 (s, 6H), 3.67 (s, 3H), 1.97 (d, J=5.1 Hz, 3H). MS: 407.4 (M+H).

EXAMPLE 3

1-Benzyl-6-(3-4,5-trimethoxyphenyl)-1,3-dihydroimidazo[4,5-b]pyrazin-2-one (Compound 3)

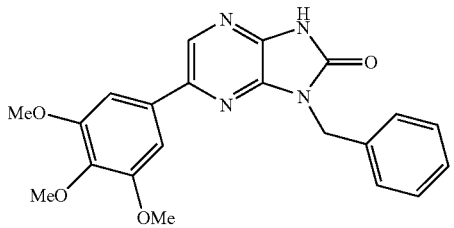

Prepared according to the procedure described for Example 1, in 35% overall yield. $^1$H NMR (300 MHz, DMSO): δ 12.10 (s, 1H), 8.54 (s, 1H), 7.43 (d, J=5.7 Hz, 2H), 7.32 (dd, J=5.7, 5.7 Hz, 2H), 7.30-7.20 (m, 3H), 5.05 (s, 2H), 3.85 (s, 6H), 3.68 (s, 3.68 (s, 3H). MS: 393.3 (M+H).

EXAMPLE 4

6-(1H-Indol-5-yl)-1-((S)-(−)-1-phenylethyl)-1,3-dihydroimidazo[4,5-b]pyrazin-2-one (Compound 4)

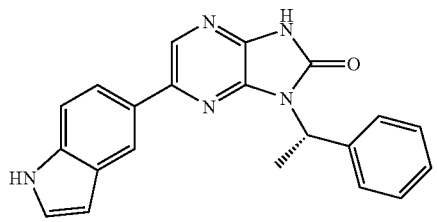

Prepared according to the procedure described for Example 1, in 29% overall yield. $^1$H NMR (300 MHz, DMSO): δ 12.00 (s, 1H), 11.20 (s, 1H), 8.46 (s, 1H), 8.17 (s, 1H), 7.74 (d, J=7.8 Hz, 1H), 7.52-7.46 (m, 3H), 7.38-7.33 (m, 3H), 7.28-7.22 (m, 1H), 6.51 (s, 1H), 5.74 (q, J=6.9 Hz, 1H), 2.04 (d, J=7.5 Hz, 3H). MS: 356.3 (M+H).

EXAMPLE 5

6-(3,5-Dimethylisoxazol-4-yl)-1-((S)-(−)-1-phenylethyl)-1,3-dihydro-imidazo[4,5-b]pyrazin-2-one (Compound 5)

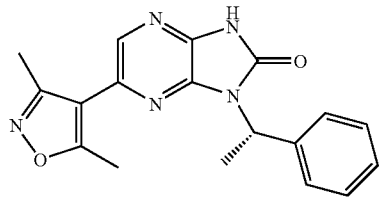

Prepared according to the procedure described for Example 1, in 27% overall yield. $^1$H NMR (300 MHz, DMSO): δ 8.01 (s, 1H), 7.70 (d, J=6.0 Hz, 2H), 7.31 (dd, J=5.7, 5.6 Hz, 2H), 7.25-7.23 (m, 1H), 5.67 (q, J=5.1 Hz, 1H), 2.45 (s, 3H), 2.24 (s, 3H), 1.92 (d, J=5.1 Hz, 3H). MS: 336.0 (M+H).

EXAMPLE 6

3-[2-Oxo-3-((S)-(−)-1-phenylethyl)-2,3-dihydro-1H-imidazo[4,5-b]pyrazin-5-yl]benzonitrile (Compound 6)

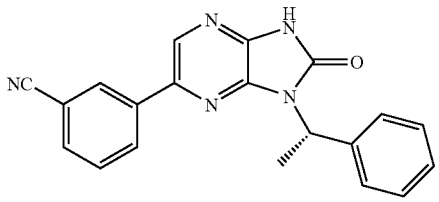

Prepared according to the procedure described for Example 1, in 27% overall yield. $^1$H NMR (300 MHz, DMSO): δ 12.10 (s, 1H), 8.64 (s, 1H), 8.41 (s, 1H), 8.34 (d, J=8.1 Hz, 1H), 7.85 (d, J=7.5 Hz, 1H), 7.69 (dd, J=8.1, 8.0 Hz, 1H), 7.50 (d, J=7.2 Hz, 2H), 7.35 (dd, J=7.5, 7.5 Hz, 2H), 7.29-7.25 (m, 1H), 5.75 (q, J=7.2 Hz, 1H), 2.00 (d, J=7.2 Hz, 3H). MS: 342.3 (M+H).

EXAMPLE 7

6-(3-Hydroxymethylphenyl)-1-((S)-(−)-1-phenylethyl)-1,3-dihydro-imidazo[4,5-b]pyrazin-2-one (Compound 7)

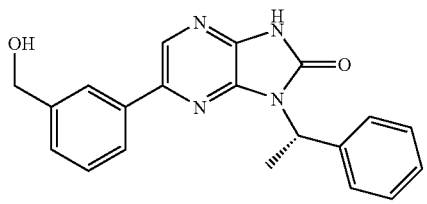

Prepared according to the procedure described for Example 1, in 27% overall yield. ¹H NMR (300 MHz, DMSO): δ 12.10 (s, 1H), 8.47 (s, 1H), 7.93 (s, 1H), 7.85 (d, J=7.5 Hz, 1H), 7.51-7.26 (m, 7H), 5.73 (q, J=7.5 Hz, 1H), 5.28 (t, J=5.7 Hz, 1H), 4.57 (d, J=5.7 Hz, 2H), 2.01 (d, J=7.2 Hz, 3H). MS: 347.2 (M+H).

EXAMPLE 8

6-(1H-Indol-2-yl)-1-((S)-(−)-1-phenylethyl)-1,3-dihydro-imidazo[4,5-b]pyrazin-2-one (Compound 8)

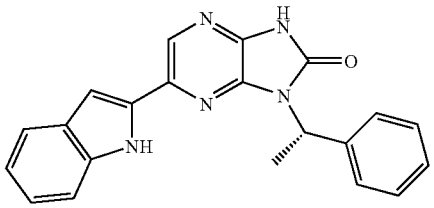

Prepared according to the procedure described for Example 1, in 15% overall yield. ¹H NMR (300 MHz, DMSO): δ 12.08 (s, 1H), 11.45 (s, 1H), 8.55 (s, 1H), 7.58-7.54 (m, 2H), 7.48 (d, J=8.4 Hz, 1H), 7.37-7.32 (m, 2H), 7.28-7.26 (m, 1H), 7.14-7.08 (m, 3H), 7.03-6.98 (m, 1H), 5.79 (q, J=7.5 Hz, 1H), 2.08 (d, J=7.5 Hz, 3H). MS: 356.1 (M+H).

EXAMPLE 9

1-Benzyl-6-pyridin-3-yl-1,3-dihydroimidazo[4,5-b]pyrazin-2-one (Compound 9)

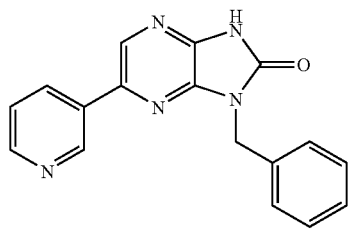

Prepared according to the procedure described for Example 1, in 18% overall yield. ¹H NMR (300 MHz, DMSO): δ 12.25 (s, 1H), 9.22 (d, J=2.1 Hz, 1H), 8.61 (s, 1H), 8.59 (dd, J=1.5, 4.8 Hz, 1H), 8.37 (td, J=1.5, 8.4 Hz, 1H), 7.53-7.28 (m, 6H), 5.09 (s, 2H). MS: 304.1 (M+H).

EXAMPLE 10

1-Benzyl-6-(3,4-dimethoxyphenyl)-1,3-dihydroimidazo[4,5-b]pyrazin-2-one (Compound 10)

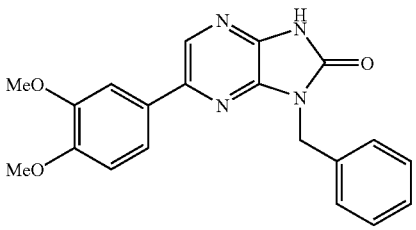

Prepared according to the procedure described for Example 1, in 35% overall yield. ¹H NMR (300 MHz, DMSO): δ 12.10 (s, 1H), 8.49 (s, 1H), 7.58 (d, J=7.5 Hz, 1H), 7.43 (d, J=7.5 Hz, 1H), 7.56-7.27 (m, 5H), 7.04 (d, J=7.8 Hz, 1H), 5.07 (s, 2H), 3.85 (s, 3H), 3.79 (s, 3H). MS: 363.2 (M+H).

EXAMPLE 11

1-Benzyl-6-(6-methoxypyridin-3-yl)-1,3-dihydroimidazo[4,5-b]pyrazin-2-one (Compound 11)

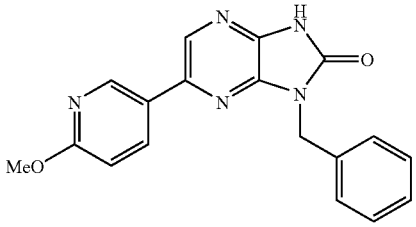

Prepared according to the procedure described for Example 1, in 12% overall yield. ¹H NMR (300 MHz, DMSO): δ 12.20 (s, 1H), 8.59 (s, 1H), 8.24-8.21 (m, 2H), 7.41-7.27 (m, 5H), 7.17 (dd, J=5.4, 7.2 Hz, 1H), 5.06 (s, 2H), 3.97 (s, 3H). MS: 334.1 (M+H).

EXAMPLE 12

1-Benzyl-6-(3-methoxymethylphenyl)-1,3-dihydroimidazo[4,5-b]pyrazin-2-one (Compound 12)

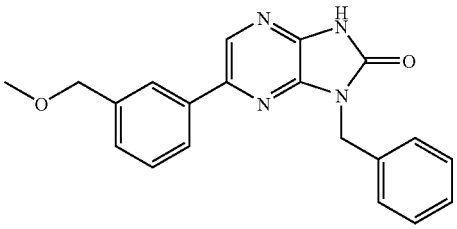

Prepared according to the procedure described for Example 1, in 29% overall yield. ¹H NMR (300 MHz, DMSO): δ 12.20 (s, 1H), 8.51 (s, 1H), 7.95-7.92 (m, 2H), 7.45-7.27 (m, 7H), 5.07 (s, 2H), 4.48 (s, 2H), 3.32 (s, 3H). MS: 347.1 (M+H).

EXAMPLE 13

6-(3-Acetylphenyl)-1-benzyl-1,3-dihydroimidazo[4,5-b]pyrazin-2-one (Compound 13)

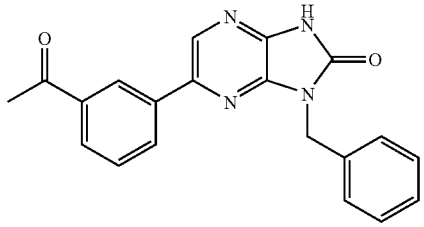

Prepared according to the procedure described for Example 1, in 21% overall yield. $^1$H NMR (300 MHz, DMSO): δ 12.22 (s, 1H), 8.63 (s, 1H), 8.54 (t, J=1.8 Hz, 1H), 8.27 (td, J=1.8, 8.0 Hz, 1H), 7.97 (td, J=1.8, 8.0 Hz, 1H), 7.64 (t, J=8.0 Hz, 1H), 7.45-7.28 (m, 5H), 5.09 (s, 2H), 2.66 (s, 3H). MS: 345.1 (M+H).

EXAMPLE 14

1-Benzyl-6-(2,4-dimethoxyphenyl)-1,3-dihydroimidazo[4,5-b]pyrazin-2-one (Compound 14)

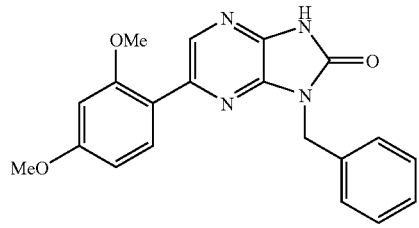

Prepared according to the procedure described for Example 1, in 29% overall yield. $^1$H NMR (300 MHz, DMSO): δ 12.04 (s, 1H), 8.38 (s, 1H), 7.68 (d, J=9.3 Hz, 1H), 7.40-7.27 (m, 5H), 6.68-6.65 (m, 2H), 5.04 (s, 2H), 3.84 (s, 3H), 3.81 (s, 3H). MS: 363.1 (M+H).

EXAMPLE 15

1-Benzyl-6-thiophen-3-yl-1,3-dihydroimidazo[4,5-b]pyrazin-2-one (Compound 15)

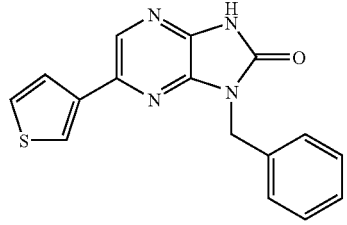

Prepared according to the procedure described for Example 1, in 30% overall yield. $^1$H NMR (300 MHz, DMSO): δ 12.10 (s, 1H), 8.45 (s, 1H), 8.09-8.05 (m, 1H), 7.73-7.64 (m, 2H), 7.43-7.27 (m, 5H), 5.05 (s, 2H). MS: 309.0 (M+H).

EXAMPLE 16

1-Benzyl-6-thiophen-2-yl-1,3-dihydroimidazo[4,5-b]pyrazin-2-one (Compound 16)

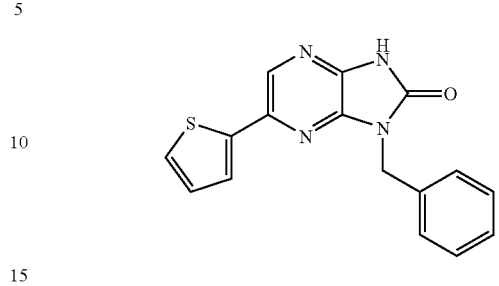

Prepared according to the procedure described for Example 1, in 27% overall yield. $^1$H NMR (400 MHz, DMSO): δ 12.11 (s, 1H), 8.45 (s, 1H), 7.70 (dd, J=1.2, 3.6 Hz, 1H), 7.57 (dd, J=0.8, 4.8 Hz, 1H), 7.40 (d, J=7.2 Hz, 2H), 7.33 (dd, J=7.2, 8.4 Hz, 2H), 7.28-7.24 (m, 1H), 7.12 (dd, J=3.6, 4.8 Hz, 1H), 5.00 (s, 2H). MS: 309.0 (M+H).

EXAMPLE 17

1-Benzyl-6-(3-methoxyphenyl)-1,3-dihydroimidazo[4,5-b]pyrazin-2-one (Compound 17)

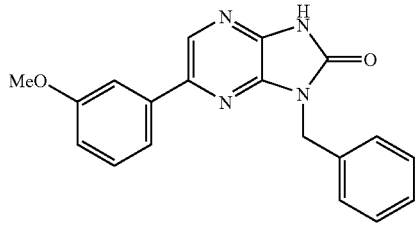

Prepared according to the procedure described for Example 1, in 33% overall yield. $^1$H NMR (400 MHz, DMSO): δ 12.11 (s, 1H), 8.51 (s, 1H), 7.58-7.53 (m, 2H), 7.42-7.24 (m, 6H), 6.95 (dd, J=2.4, 7.2 Hz, 1H), 5.06 (s, 2H), 3.81 (s, 3H). MS: 333.0 (M+H).

EXAMPLE 18

3-(3-Benzyl-2-oxo-2,3-dihydro-1H-imidazo[4,5-b]pyrazin-5-yl)benzoic acid (Compound 18)

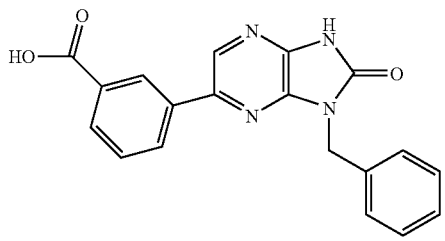

Prepared according to the procedure described for Example 1, in 16% overall yield. $^1$H NMR (400 MHz, DMSO): δ 13.12 (s, 1H), 12.20 (s, 1H), 8.58 (s, 1H), 8.56 (t, J=2.0 Hz, 1H), 8.25 (td, J=2.9, 11.2 Hz, 1H), 7.96 (td, J=2.9, 11.2 Hz, 1H), 7.61 (t, J=10.4 Hz, 1H), 7.44-7.25 (m, 5H), 5.09 (s, 2H). MS: 347.0 (M+H).

EXAMPLE 19

1-Pyridin-2-ylmethyl-6-(3,4,5-trimethoxyphenyl)-1,3-dihydroimidazo[4,5-b]pyrazin-2-one (Compound 19)

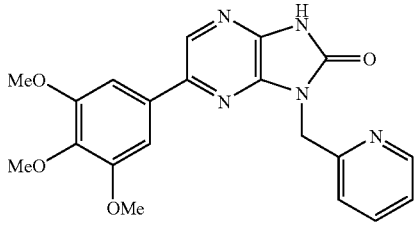

Prepared according to the procedure described for Example 1, in 20% overall yield. $^1$H NMR (300 MHz, DMSO): δ 12.17 (s, 1H), 8.60 (s, 1H), 8.45 (d, 1H), 7.80 (t, 1H), 7.45 (d, 1H), 7.30 (t, 1H), 7.20 (s, 2H), 5.20 (s, 2H), 3.80 (s, 6H), 3.67 (s, 3H). MS: 394.1 (M+H).

EXAMPLE 20

1-Pyridin-3-yl methyl-6-(3,4,5-trimethoxyphenyl)-1,3-dihydroimidazo-[4,5-b]pyrazin-2-one (Compound 20)

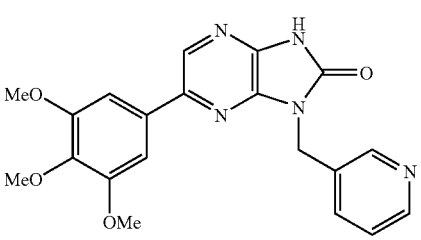

Prepared according to the procedure described for Example 1, in 20% overall yield. $^1$H NMR (300 MHz, DMSO): δ 12.17 (s, 1H), 8.87 (s, 1H), 8.67 (d, 1H), 8.60 (s, 1H), 8.17 (d, 1H), 7.65 (t, 1H), 7.28 (s, 2H), 5.20 (s, 2H), 3.87 (s, 6H), 3.70 (s, 3H). MS: 394.0 (M+H).

EXAMPLE 21

1-Benzyl-6-(3,5-dimethoxyphenyl)-1,3-dihydro-imidazo[4,5-b]pyrazin-2-one (Compound 21)

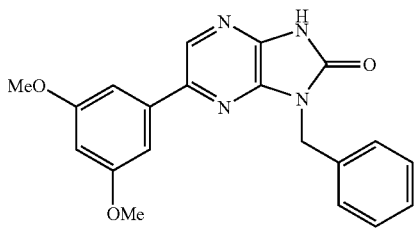

Prepared according to the procedure described for Example 1, in 25% overall yield. $^1$H NMR (300 MHz, CDCl$_3$): δ 7.59-7.57 (m, 2H), 7.39-7.26 (m, 4H), 7.12 (d, J=2.1 Hz, 2H), 6.54 (t, J=2.1 Hz, 1H), 5.19 (s, 2H), 3.89 (s, 6H). MS: 363.3 (M+H).

EXAMPLE 22

5-(3-Benzyl-2-oxo-2,3-dihydro-1H-imidazo[4,5-b]pyrazin-5-yl)-2-methoxybenzaldehyde (Compound 22)

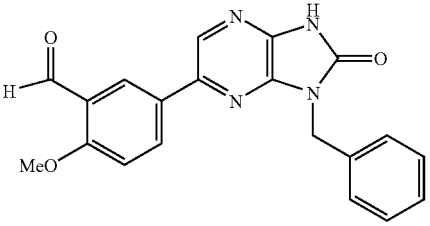

Prepared according to the procedure described for Example 1, in 40% overall yield. $^1$H NMR (400 MHz, CDCl$_3$): δ 10.44 (s, 1H), 8.62 (s, 1H), 8.42 (d, J=2.4 Hz, 1H), 8.38 (s, 1H), 8.21 (dd, J=2.4, 8.8 Hz, 1H), 7.58-7.56 (m, 2H), 7.38-7.27 (m, 3H), 7.14 (d, J=8.8 Hz, 1H), 5.19 (s, 2H), 4.02 (s, 3H). MS: 361.0 (M+H).

EXAMPLE 23

5-(3-Benzyl-2-oxo-2,3-dihydro-1H-imidazo[4,5-b]pyrazin-5-yl)-2-methoxybenzoic acid (Compound 23)

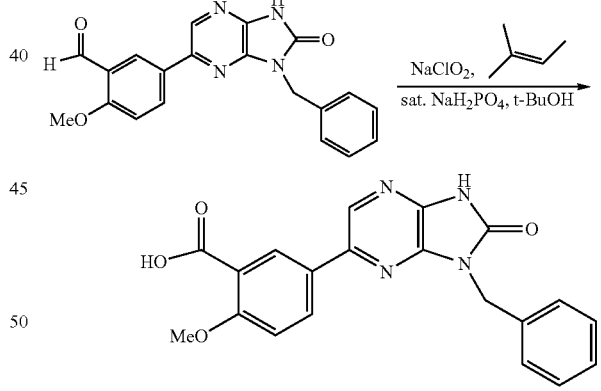

To a solution of 5-(3-Benzyl-2-oxo-2,3-dihydro-1H-imidazo[4,5-b]pyrazin-5-yl)-2-methoxybenzaldehyde (296 mg, 0.82 mmol) in t-BuOH (18.2 mL) was sequentially added saturated aqueous NaH$_2$PO$_4$ solution (4.1 mL), 2-methyl-2-butene (2M in THF, 3.92 mL) and NaClO$_2$ (114.8 mg). The mixture was stirred at room temperature for one hour, and then concentrated under reduced pressure. The residue thus obtained was purified by column chromatography [silica gel; MeOH/DCM (1:9)] to give the product as white powder (244 mg, 65%). $^1$H NMR (400 MHz, DMSO): δ 8.44 (s, 1H), 8.19 (s, 1H), 8.08 (d, J=9.2 Hz, 1H), 7.40-7.26 (m, 5H), 7.18 (d, J=8.8 Hz, 1H), 5.05 (s, 2H), 3.84 (s, 3H). MS: 377.0 (M+H).

EXAMPLE 24

1-Benzyl-6-(3-hydroxymethyl-4-methoxyphenyl)-1,3-dihydro-imidazo[4,5-b]pyrazin-2-one (Compound 24)

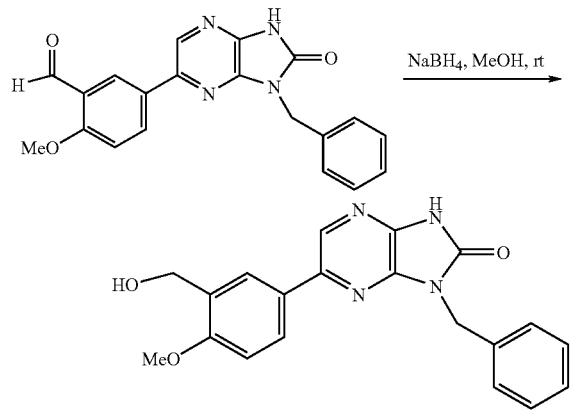

To a solution of 5-(3-Benzyl-2-oxo-2,3-dihydro-1H-imidazo[4,5-b]pyrazin-5-yl)-2-methoxybenzaldehyde (27.2 mg, 0.076 mmol) in MeOH (1 mL) was added NaBH$_4$ (2.86 mg, 0.076 mmol). The mixture was stirred at room temperature for one hour, and then concentrated under reduced pressure. The residue thus obtained was purified by column chromatography [silica gel; MeOH/DCM (1:19)] to give the product as an off-white powder (22 mg, 80%). $^1$H NMR (400 MHz, DMSO): δ 8.35 (s, 1H), 8.01 (s, 1H), 7.84 (dd, J=2.0, 8.8 Hz, 1H), 7.40-7.25 (m, 5H), 7.02 (d, J=8.4 Hz, 1H), 5.04 (s, 2H), 4.52 (d, J=5.2 Hz, 2H), 3.81 (s, 3H). MS: 363.0 (M+H).

EXAMPLE 25

5-(3-Benzyl-2-oxo-2,3-dihydro-1H-imidazo[4,5-b]pyrazin-5-yl)-2-hydroxybenzoic acid (Compound 25)

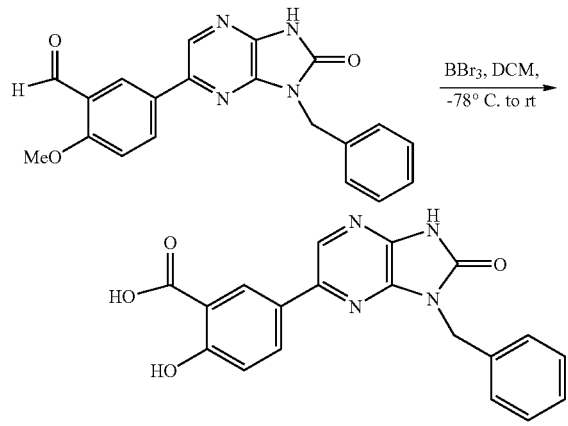

To a suspension of 5-(3-Benzyl-2-oxo-2,3-dihydro-1H-imidazo[4,5-b]pyrazin-5-yl)-2-methoxybenzoic acid (105.9 mg, 0.282 mmol) in DCM (10 mL) at −78° C. was added BBr$_3$ (1 M in DCM, 0.563 mL, 0.563 mmol) in a dropwise fashion. The mixture was allowed to warm to room temperature and stirred vigorously for 16 hours. After concentration under reduced pressure, the residue thus obtained was purified by column chromatography [silica gel; MeOH/DCM (1:9)] to give the product as a brown powder (82 mg, 80%). $^1$H NMR (400 MHz, DMSO): δ 12.02 (s, 1H), 8.34-8.33 (m, 2H), 7.87 (dd, J=3.0, 11.6 Hz, 1H), 7.41-7.27 (m, 5H), 6.77 (d, J=12.0 Hz, 1H), 5.07 (s, 2H). MS: 363.1 (M+H).

EXAMPLE 26

5-(3-Benzyl-2-oxo-2,3-dihydro-1H-imidazo[4,5-b]pyrazin-5-yl)-2-methoxybenzamide (Compound 26)

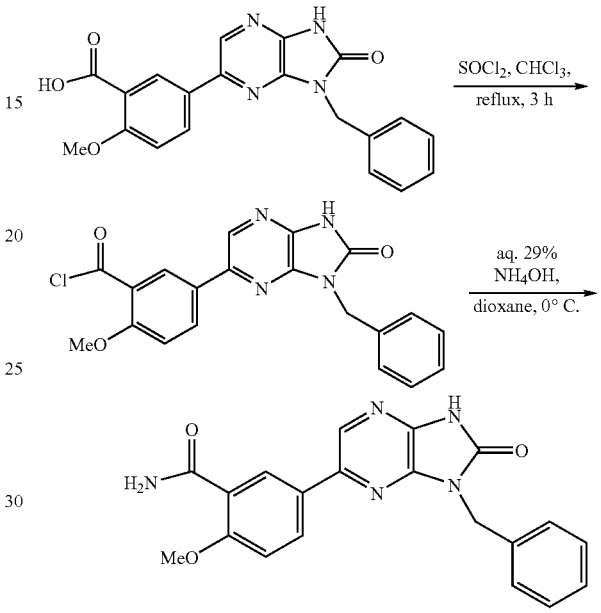

To a solution of 5-(3-Benzyl-2-oxo-2,3-dihydro-1H-imidazo[4,5-b]pyrazin-5-yl)-2-methoxybenzoic acid (78.3 mg, 0.21 mmol) in CHCl$_3$ (2 mL) was added SOCl$_2$ (0.06 mL, 0.83 mmol). The mixture was heated to reflux and stirred for 3 hours. After cooling to room temperature and removal of solvents under reduced pressure, the residue was treated with toluene (2 mL) and concentrated. This crude acid chloride was dissolved in dioxane (0.8 mL), cooled to 0° C. and treated with aqueous NH$_4$OH solution (29%; 0.3 mL) in a dropwise fashion. After stirring for 10 minutes, the mixture was concentrated under reduced pressure. The residue thus obtained was purified by column chromatography [silica gel; MeOH/DCM (1:9)] to give the product as a yellow powder (39 mg, 50% over 2 steps). $^1$H NMR (300 MHz, DMSO): δ 8.44 (s, 1H), 8.40 (d, J=2.1 Hz, 1H), 8.12-8.08 (m, 1H), 7.69-7.59 (m, 2H), 7.42-7.22 (m, 6H), 5.07 (s, 2H), 3.93 (s, 3H). MS: 376.0 (M+H).

EXAMPLE 27

1-(3-Nitrobenzyl)-6-(3,4,5-trimethoxyphenyl)-1,3-dihydroimidazo[4,5-b]pyrazin-2-one (Compound 27)

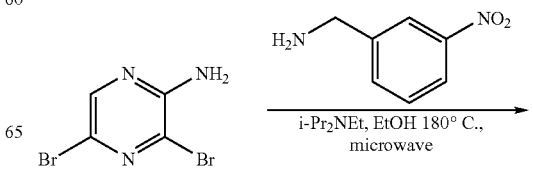

-continued

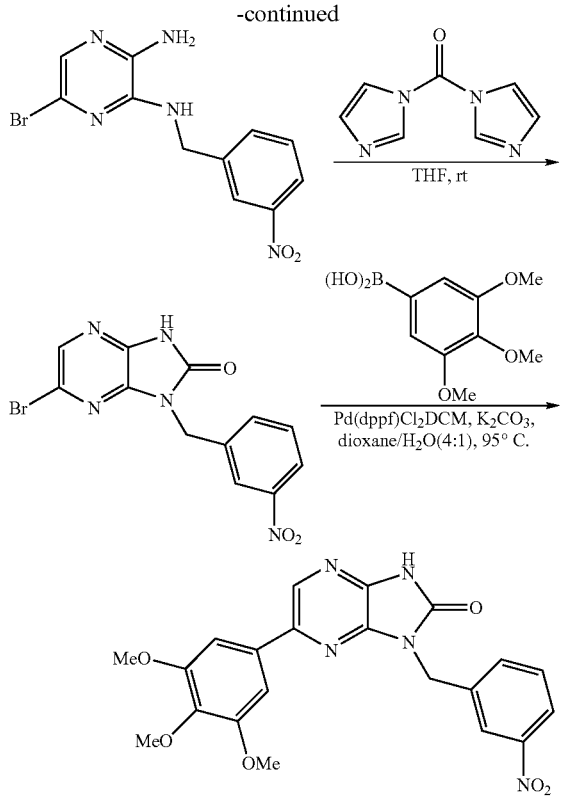

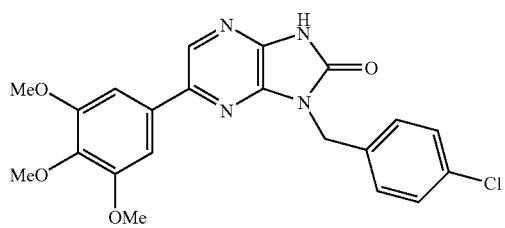

To a solution of 3,5-dibromopyrazin-2-ylamine (253 mg, 1.0 mmol), diisopropylethyl-amine (0.2 mL, 1.5 mmol) and anhydrous ethanol (2 mL) in a microwave tube (Smith process vial, 2-5 mL) was added m-nitrobenzylamine (192 mg, 1.2 mmol). The tube was sealed and heated at 180° C. in a microwave reactor (Smith Synthesizer) for 1.5 h. The reaction mixture was then concentration under reduced pressure and the resultant residue was purified by flash chromatography [silica gel, hexanes/ethyl acetate (2:1)] to afford 5-bromo-$N^3$-(3-nitrobenzyl)pyrazine-2,3-diamine as a brown solid (100 mg, 31%).

To a solution of 5-bromo-$N^3$-(3-nitrobenzyl)pyrazine-2,3-diamine (100 mg, 0.31 mmol) in anhydrous tetrahydrofuran (10 mL) was added diimidazol-1-ylmethanone (250 mg, 1.51 mmol) at room temperature. After stirring overnight, the reaction was concentrated under reduced pressure. Purification of the resultant residue by flash chromatography [silica gel; hexanes/ethyl acetate (2:1)] afforded 6-bromo-1-(3-nitrobenzyl)-1,3-dihydroimidazo[4,5-b]pyrazin-2-one as a red-brown solid (95 mg, 88%).

To a solution of 6-bromo-1-(3-nitrobenzyl)-1,3-dihydroimidazo[4,5-b]pyrazin-2-one (95 mg, 0.27 mmol), 3,4,5-trimethoxyphenyl boronic acid (65 mg, 0.30 mmol) and potassium carbonate (120 mg, 0.88 mmol) in degassed 20% aq. dioxane (2.5 mL) was added dichloro[1,1'-bis(diphenylphosphino)ferrocene]palladium(II) dichloromethane adduct (24 mg, 0.029 mmol) under an argon atmosphere. The mixture was stirred at 95° C. overnight, then cooled to room temperature and concentrated under reduced pressure. Purification of the resultant residue by flash chromatography [silica gel; hexanes/ethyl acetate (2:1)] afforded 1-(3-nitrobenzyl)-6-(3,4,5-trimethoxyphenyl)-1,3-dihydroimidazo[4,5-b]pyrazin-2-one as a white solid (82 mg, 70%). $^1$H NMR (300 MHz, CDCl$_3$): δ 8.48 (t, J=2.2 Hz, 1H), 8.19 (dd, J=7.5 and 2.2 Hz, 1H), 7.91 (dd, J=7.5 and 2.2 Hz, 1H), 7.55 (t, J=7.5 Hz, 1H), 7.16 (s, 2H), 5.30 (s, 2H), 4.00 (s, 6H), 3.92 (s, 3H). MS: 438.1 (M+H).

EXAMPLE 28

1-(4-Chlorobenzyl)-6-(3,4,5-trimethoxyphenyl)-1,3-dihydro-imidazo[4,5-b]pyrazin-2-one (Compound 28)

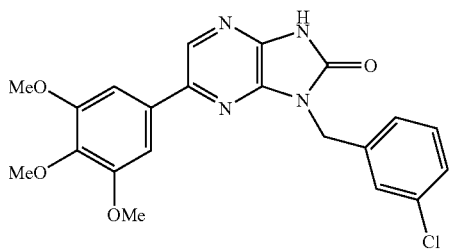

Prepared according to the procedure described for Example 27, in 40% overall yield. $^1$H NMR (300 MHz, CDCl$_3$): δ 10.38 (br, 1H), 8.37 (s, 1H), 7.50 (d, J=8.5 Hz, 2H), 7.30 (d, J=8.5 Hz, 2H), 7.16 (s, 2H), 5.17 (s, 2H), 3.98(s, 6H), 3.92 (s, 3H). MS: 427.1 (M+H).

EXAMPLE 29

1-(3-Chlorobenzyl)-6-(3,4,5-trimethoxyphenyl)-1,3-dihydro-imidazo[4,5-b]pyrazin-2-one (Compound 29)

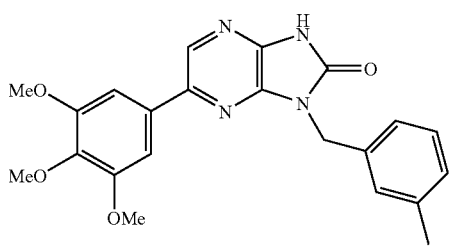

Prepared according to the procedure described for Example 27, in 25% overall yield. $^1$H NMR (300 MHz, CDCl$_3$): δ 10.38 (br, 1H), 8.37 (s, 1H), 7.72-7.43 (m, 3H), 7.30 (s, 1H), 7.17 (s, 2H), 5.17 (s, 2H), 3.99 (s, 6H), 3.92 (s, 3H). MS: 427.1 (M+H).

EXAMPLE 30

1-(3-Methylbenzyl)-6-(3,4,5-trimethoxyphenyl)-1,3-dihydro-imidazo[4,5-b]pyrazin-2-one (Compound 30)

Prepared according to the procedure described for Example 27, in 35% overall yield. $^1$H NMR (300 MHz, CDCl$_3$): δ 10.22 (br, 1H), 8.36 (s, 1H), 7.40 (d, J=7.2 Hz, 1H), 7.37 (s, 1H), 7.22 (t, J=7.2 Hz, 1H), 7.20 (s, 2H), 7.10 (d, J=7.2 Hz, 1H), 5.17 (s, 2H), 3.99 (s, 6H), 3.92 (s, 3H), 2.32 (s, 3H). MS: 407.1 (M+H).

EXAMPLE 31

1-(3-Fluorobenzyl)-6-(3,4,5-trimethoxyphenyl)-10,3-dihydro-imidazo[4,5-b]pyrazin-2-one (Compound 31)

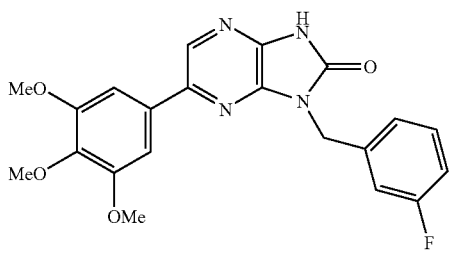

Prepared according to the procedure described for Example 27, in 20% overall yield. $^1$H NMR (300 MHz, CDCl$_3$): δ 9.70 (br, 1H), 8.36 (s, 1H), 7.40-7.28 (m, 3H), 7.16 (s, 2H), 7.00 (m, 1H), 5.18 (s, 2H), 3.98 (s, 6H), 3.92 (s, 3H). MS: 411.1 (M+H).

EXAMPLE 32

1-(3-Methoxybenzyl)-6-(3,4,5-trimethoxyphenyl)-1,3-dihydro-imidazo[4,5-b]pyrazin-2-one (Compound 32)

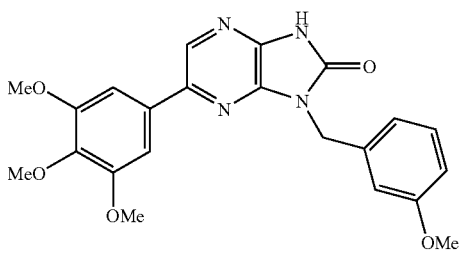

Prepared according to the procedure described for Example 27, in 15% overall yield. $^1$H NMR (300 MHz, CDCl$_3$): δ 9.98 (br, 1H), 8.35 (s, 1H), 7.25 (m, 1H), 7.19 (s, 2H), 7.14 (m, 2H), 6.83 (m, 1H), 5.17 (s, 2H), 3.99 (s, 6H), 3.92 (s, 3H), 3.77 (s, 3H). MS: 423.1 (M+H).

EXAMPLE 33

1-Naphthalen-1-ylmethyl-6-(3,4,5-trimethoxyphenyl)-1,3-dihydro-imidazo[4,5-b]pyrazin-2-one (Compound 33)

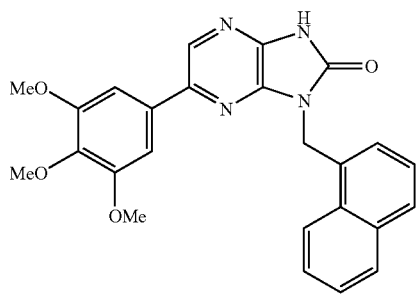

Prepared according to the procedure described for Example 27, in 21% overall yield. $^1$H NMR (300 MHz, CDCl$_3$): δ 10.44 (br, 1H), 8.57 (d, J=8.5 Hz, 1H), 8.35 (s, 1H), 7.88-7.82 (m, 3H), 7.61-7.41 (m, 3H), 7.15 (s, 2H), 5.66 (s, 2H), 3.97 (s, 6H), 3.92 (s, 3H). MS: 443.1 (M+H).

EXAMPLE 34

1-Benzo[1,3]dioxol-5-ylmethyl-6-(3,4,5-trimethoxyphenyl)-1,3-dihydroimidazo[4,5-b]pyrazin-2-one (Compound 34)

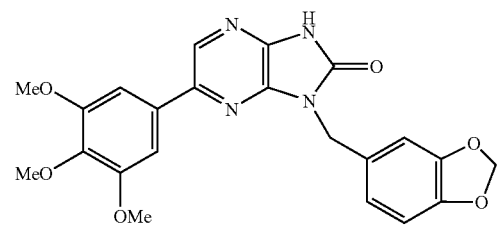

Prepared according to the procedure described for Example 27, in 20% overall yield. $^1$H NMR (300 MHz, CDCl$_3$): δ 9.05 (br, 1H), 8.33 (s, 1H), 7.19 (s, 2H), 7.12 (d, J=1.5 Hz, 1H), 7.06 (dd, J=7.9 and 1.5 Hz, 1H), 6.75 (d, J=7.9 Hz, 1H), 5.92 (s, 2H), 5.09 (s, 2H), 3.99 (s, 6H), 3.92 (s, 3H). MS: 437.0 (M+H).

EXAMPLE 35

1-Indan-1-yl-6-(3,4,5-trimethoxyphenyl)-1,3-dihydroimidazo[4,5-b]pyrazin-2-one (Compound 35)

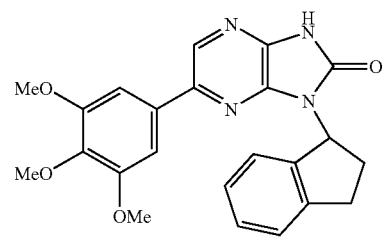

Prepared according to the procedure described for Example 27, in 10% overall yield. $^1$H NMR (300 MHz, CDCl$_3$): δ 9.71 (br, 1H), 8.31 (s, 1H), 7.32-7.16 (m, 4H), 6.92 (s, 2H), 6.20 (m, 1H), 3.88 (s, 9H), 3.53 (m, 1H), 3.10 (m, 1H), 2.68 (m, 2H). MS: 419.0 (M+H).

EXAMPLE 36

1-Thiophen-2-ylmethyl-6-(3,4,5-tri methoxyphenyl)-1,3-dihydro-imidazo[4,5-b]pyrazin-2-one (compound 36)

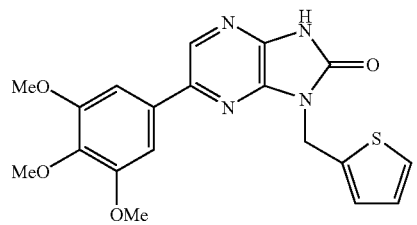

Prepared according to the procedure described for Example 27, in 10% overall yield. $^1$H NMR (300 MHz, CDCl$_3$): δ 8.23 (s, 1H), 7.20-7.16 (m, 4H), 6.88 (dd, J=5.1 and 3.5 Hz, 1H), 5.28 (s, 2H), 3.92 (s, 6H), 3.84 (s, 3H). MS: 399.0 (M+H).

EXAMPLE 37

1-(2-Chlorobenzyl)-6-(3,4,5-trimethoxyphenyl)-1,3-dihydro-imidazo[4,5-b]pyrazin-2-one (compound 37)

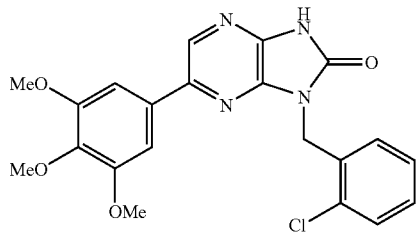

Prepared according to the procedure described for Example 27, in 25% overall yield. $^1$H NMR (300 MHz, CDCl$_3$): δ 8.89 (br, 1H), 8.36 (s, 1H), 7.43 (m, 2H), 7.23 (m, 2H), 7.15 (s, 2H), 5.36 (s, 2H), 3.95 (s, 6H), 3.89 (s, 3H). MS: 427.0 (M+H).

EXAMPLE 38

1-(4-Aminobenzyl)-6-(3,4,5-trimethoxyphenyl)-1,3-dihydroimidazo[4,5-b]pyrazin-2-one (compound 38)

To a mixture of 1-(4-chlorobenzyl)-6-(3,4,5-trimethoxyphenyl)-1,3-dihydro-imidazo[4,5-b]pyrazin-2-one (19 mg, 0.04 mmol; Example 28), benzhydrylideneamine (16 mg, 0.08 mmol), Pd$_2$(dba)$_3$ (7 mg, 0.007 mmol), and (9,9-dimethyl-9H-xanthene-4,5-diyl0bis[diphenylphosphine] also known as XantPhos (13 mg, 0.027 mmol) in toluene (0.5 mL) was added sodium tert-butoxide (10 mg; 0.1 mmol) and the resultant mixture was heated to 95° C. overnight. After cooling to room temperature, the reaction was diluted with water and extracted with EtOAc. Concentration of the organic phase under reduced pressure afforded a crude residue, which was purified by silica gel chromatography [EtOAc/hexane (3:2)] to afford 1-[4-(benzhydrylidene-amino)benzyl]-6-(3,4,5-trimethoxyphenyl)-1,3-dihydroimidazo[4,5-b]pyrazin-2-one (14 mg) as a yellow oil.

1-[4-(Benzhydrylideneamino)benzyl]-6-(3,4,5-trimethoxyphenyl)-1,3-dihydroimidazo[4,5-b]pyrazin-2-one (10 mg, 0.0175 mmol) was dissolved in THF (0.5 mL) and 4N aq. HCl (0.3 mL) was added. The mixture was stirred overnight at room temperature, concentrated under reduced pressure, and the resultant residue was purified by silica gel chromatography [EtOAc] to afford 1-(4-aminobenzyl)-6-(3,4,5-trimethoxyphenyl)-1,3-dihydroimidazo[4,5-b]pyrazin-2-one (1.8 mg, 20% overall yield) as a yellow solid. $^1$H NMR (300 MHz, CDCl$_3$): δ 8.90 (br, 1H), 8.32 (s, 1H), 7.40 (d, J=8.1 Hz, 2H), 7.19 (s, 2H), 6.62 (d, J=8.1 Hz, 2H), 5.08 (s, 2H), 3.99 (s, 6H), 3.92 (s, 3H). MS: 408.1 (M+H).

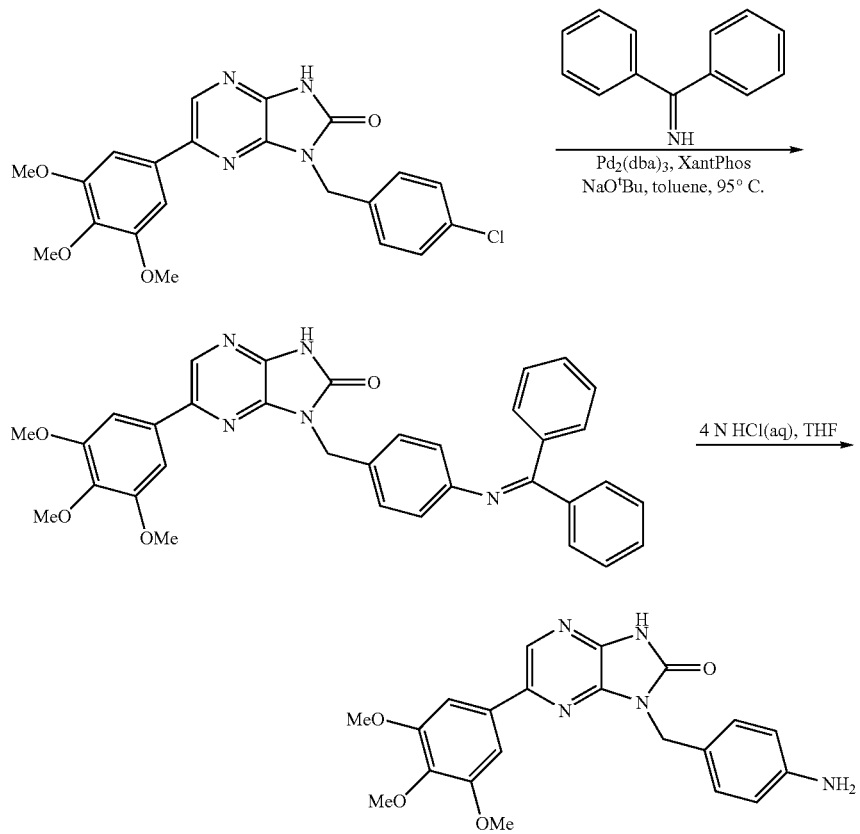

EXAMPLE 39

1-(3-Aminobenzyl)-6-(3,4,5-tri methoxyphenyl)-1,3-dihydro-imidazo[4,5-b]pyrazin-2-one (compound 39)

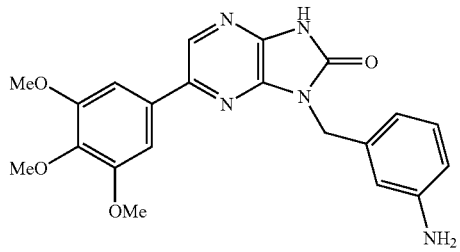

Prepared from 1-(3-chlorobenzyl)-6-(3,4,5-tri methoxyphenyl)-1,3-dihydroimidazo[4,5-b]pyrazin-2-one (Example 29) according to the procedure described for Example 38, in 10% overall yield. $^1$H NMR (300 MHz, CDCl$_3$): δ 9.4 (br, 1H), 8.34 (s, 1H), 7.19 (s, 2H), 7.10 (t, J=7.6 Hz, 1H), 6.98 (dd, J=7.6 and 2.1 Hz, 1H), 6.85 (t, J=2.1 Hz, 1H), 6.59 (dd, J=7.6 and 2.1 Hz, 1H), 5.10 (s, 2H), 3.98 (s, 6H), 3.91 (s, 3H). MS: 408.1 (M+H).

IV. Pharmacological Examples

In vitro assays were run to measure potency of Aurora-2 kinase inhibition by selected compounds of Formula I.

Aurora-2 Enzymatic Assay. An ELISA-based enzymatic assay was used to determine the compound potency for Aurora-2. In this assay, phosphorylated Aurora-2 (Pi-Aurora-2) catalyzes the ATP-dependent phosphorylation of Ser-10 of Histone H3. Pi-Aurora-2 was produced by autophosphorylation of Aurora-2 (residues 125-391) by 1 mM ATP in the presence of 10 mM MgCl$_2$. The assay buffer used was 100 mM HEPES, pH 7.5, 1 mM DTT, 0.01% (v/v) Tween-20. Compounds were diluted in assay buffer containing 4% DMSO just prior to the assay.

Procedure. High-binding 96-well ELISA plates (Costar 9018) were coated overnight at 4° C. with 10 μg/ml human Histone H3 (Upstate) in PBS (100 μl/well). The following day, the plates were emptied and blocked with 1% BSA in PBS (150 μl/well) for 1 h at 37° C. At the end of the incubation, plates were washed 3 times with 0.01% Tween-20 in PBS (300 μl/well). 50 μl of compound were dispensed to each well followed by addition of 20 μl 10 mM MgCl$_2$ and 20 μl 50 μM ATP (Sigma). The reaction was initiated by addition of 10 μl 30 nM Pi-Aurora-2. Control reactions were run in each plate: in positive and negative control wells, assay buffer (made 4% in DMSO) was substituted for the compound; in addition, positive control wells did not receive Pi-Aurora-2.

The plates were incubated at room temperature for 30 min. The reaction was quenched with 9 μl 50 mM EDTA and the plates were washed 5 times with 0.01% Tween-20 in PBS (300 μl/well). The phospho-histone H3 (Ser10) 6G3 monoclonal antibody (Cell Signaling) was then diluted 2,000-fold with 1% BSA in PBS, and was added to the plates (100 μl/well). Following 1 h incubation at 37° C., the plates were washed as described above. The HRP-conjugated secondary antibody (goat anti-mouse Ig(H+ L)-HRP human absorbed, Southern Biotechnology Associates, Inc.) was diluted 20,000- fold with 1% BSA in PBS and was added to the plates (100 μl/well). The plates were incubated for 1 h at 37° C. and then washed 5 times with 0.01% Tween-20 in PBS (300 μl/well). 100 μl/well TMB, SureBlue Reserve (KPL) were added. After ca. 5-6 min, each well received 100 μl 1 M HCl and the OD$_{450}$ was measured with a SpectraMax Plus microplate reader (Molecular Devices). Under these conditions, absorbance values for positive and negative controls were ca. 0.1 and 1.7, respectively, and were used to define the 100% and 0% inhibition of the Aurora-2 reaction. The IC$_{50}$ values reported (Table 1) are the averages of three independent measurements.

TABLE 1

| Compound | Aurora-2 IC$_{50}$ Enzyme (μM)* |
|---|---|
| 1 | A |
| 2 | C |
| 3 | A |
| 4 | C |
| 5 | C |
| 6 | C |
| 7 | B |
| 8 | C |
| 9 | C |
| 10 | B |
| 11 | C |
| 12 | C |
| 13 | C |
| 14 | C |
| 15 | C |
| 16 | C |
| 17 | C |
| 18 | B |
| 19 | B |
| 20 | A |
| 21 | C |
| 22 | C |
| 23 | A |
| 24 | C |
| 25 | B |
| 26 | C |
| 27 | C |
| 28 | B |
| 29 | A |
| 30 | B |
| 31 | A |
| 32 | B |
| 33 | C |
| 34 | B |
| 35 | A |
| 36 | A |
| 37 | A |
| 38 | A |
| 39 | B |

*A: <500 nM; B: >500 nM and <1 μM; C: >1 μM.

The claimed invention is:

1. A compound of Formula I:

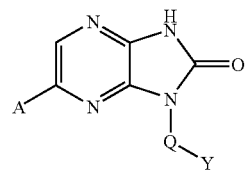

a stereoisomeric or tautomeric form thereof or a pharmaceutically acceptable salt thereof, wherein Q is a direct link or C$_{1-6}$alkylene;

Y is phenyl, naphthyl, indanyl, thienyl, pyridinyl, or benzofuranyl, each of which may be optionally substituted with one, two, or three substituents selected from the group consisting of C$_{1-4}$alkyl, nitro, amino, halogen, cyano and metboxy;

A is phenyl, pyridinyl, indolyl, isoxazolyl or thienyl, each of which may be optionally substituted with one to three substituents selected from the group consisting of C$_{1-6}$alkyl, halogen, hydroxy, hydroxyC$_{1-6}$alkyl, C$_{1-6}$alkoxy and carboxyl.

2. A compound of claim 1 wherein Q is mechylene or ethylene;
wherein Y is phenyl, indanyl, thienyl or pyridinyl; wherein A is phenyl optionally substituted with up to three substituents each independently selected from the group consisting of methyl, chioro, finoro, hydroxyrnethyl, hyciroxy, methoxy, and carboxyl.

3. A compound of claim 1 wherein the compound is 1-((S)-(–)-1-Phenylerhyl)-6-(3,4,5-trimethoxyphenyl)-1,3-dihydroimidazo[4,5-b]pyrazin-2-one;
j-((R)-(+)-I-Phenylethyl)-6-(3,4,5-trimethoxyphenyl)-1,3-dihydroimidazo[4,5-b]pyrazin-2-one;
1-Benzyl-6-(3,4,5-trimethoxyphenyl)-1,3-dihydroimidazo[4,5-b]pyrazin-2-one; 6-(1H-Indol-5-yI)-1((S)-(–)-1-phenylethyl)-1,3-dihydroimidazo[4,5-b]pyrazin-2-one;
6-(3,5-Dimethylisoxazal-4-yl)-1-((S)-(–)-1-phenylethyl)-1,3-dihydroimidazo[4,5b]pyrazin-2-one;
3-[2-Oxo-3-((S)-(–)-1-phenylethyl)-2,3-dihydro-1H-imidazo[4,5-b]pyrazin-5-yl]-benzonitrile;
6-(3-Hydroxymethylphenyl)-1-((S)-(–)-1-phenylethyl)-1,3-dihydroimidazo[4,5-b]pyrazin-2-one;
6-(1H-Indo-2-yI)-1-((S)-(–)-1-phenylethyl)-1,3-dihydroimidazo[4,5-b]pyrazin-2-one;
1-Benzyl-6-pyridia-3-yI-1,3-dihydroimidazo[4,5-b]pyrazin-2-one;
1-Benzyl-6-(3,4-dimnethoxyphenyl)-1,3-dihydroimidazo[4,5-b]pyrazin-2-one;
1-Benzyl-6-(6-methoxypyridin-3-yl)-1,3-dihydroimidazo[4,5-b]pyrazin-2-one;
1-Benzyl-6-(3.methoxymethylphenyl)-1,3-dihydroimidazol[4,5-b]pyrazin-2-one;
6-(3-Acetylphenyl)-1-benzyl-1,3-dihydroimidazo[4,5-b]pyrazin-2-one;
1-Benzyl-6-(2,4-dimethoxyphenyl)-1,3-dihydroimidazo[4,5-b]pyrazin-2-one;
1-Benzyl-6-thiophen-3-yl-1,3-dihydroimidazo[4,5-b]pyrazin-2-one;
1-Benzyl-6-thiophen-2-yl-1,3-dihydroimidazo[4,5-b]pyraz.in-2-one;
1-Benzyl-6-(3-methoxyphenyl)-1,3-dihydroimidazo[4,5-b]pyrazin-2-one;
3-(3-Benzyl-2-oxo-2,3-dihydro-1*H-imidazo*[4,5-b]pyrazin-5-yl)-benzoic acid;
1-Pyridin-2-ylmethyl-6-(3,4,5-trimethoxyphenyl)-1,3-dihydroimidazo[4,5-b]pyrazin-2-one;
1-Pyridin-3-ylmethyl-6-(3,4,5-trimethoxyphenyl)-I,3-dihydro-imidazo[4,5-b]pyrazin-2-one;
1-Benzyl-6-(3,5-dimethoxyphenyl)-1,3-dihydro-imidazo[4,5-b]pyrazin-2-one;
5-(3-Benzyl-2-oxo-2,3-dihydro-1H-imidazo[4,5-b]pyrazin-5-yl)-2-methoxybenzoic acid;
1-Benzyl-6-(3-hydroxymethyl-4-methoxyphenyl)-1,3-dihydroimidazo[4,5-b]pyrazin-2-one;
5-(3-Benzyl-2-oxo-2,3-dihydro-1H-imidazo[4,5-b]pyrazin-5-yl)-2-hydroxybenzoic acid;
1-(3-Nitrobenzyl)-6-(3,4,5-trimethoxyphenyl)-1,3-dihydroimidazo[4,5-b]pyrazin-2-one;
1-(4-Chlorobenzyl)-6-(3,4,5-trimethoxyphenyl)-1,3-dihydroimidazo[4,5-b]pyrazin-2-one;
1-(3-Chlorobenzyl)-6-(3,4,5-trimethoxyphenyl)-1,3-dihydroimidazo[4,5-b]pyrazin-2-One;
1-(3-Methylbenzyl)-6-(3,4,5-trimethoxyphenyl)-1,3-dihydroimidazo[4,5-b]pyrazin-2-one; 1-(3-Fluorobenzyl)-6-(3,4,5-trimethoxyphenyl)-1,3-dihydroimidazo[4,5-b]pyrazin-2-one;
1-(3-Methoxybenzyl)-6-(3,4,5-trimethoxyphenyl)-1,3-dihydroimidazo[4,5-b]pyrazin-2-one;
1-Naphthalen-1-ylmethyl-6-(3,4,5-trimethoxyphenyl)-1,3-dihydroimidazo[4,5-b]pyrazin-2-one;
1-Benzo[1,3]dioxol-5-ylmethyl-6-(3,4,5-trimethoxyphenyl)-1,3-dihydroimidazo[4,5-b]pyrazin-2-one;
1-Indan-1-yI-6-(3,4,5-trinaethoxyphenyl)-1,3-dihydroimidazo[4,5-b]pyrazin-2one;
1-Thiophen-2-ylmethyl-6-(3.4,5-trimethoxyphenyl)-1,3-dihydroimidazo[4,5-b]pyrazin-2-one;
1-(2-Chlorobenzyl)-6-(3,4,5trimethoxyphenyl)-1,3-dihydroimidazo[4,5-b]pyrazin-2-one;
1-(4-Aminobenzyl)-6-(3,4,5-trimethoxypheflyl)-1,3-dihydroimidazo[4,5-b]pyrazin-2-one,
1-(3-Aminobenzyl)-6-(3,4,5-trimethoxyphenyl)-1,3-dihydroimidazo[4,5-b]pyrazin-2-one; or a pharmaceutically acceptable salt thereof.

4. A compound of claim 1 wherein the compound is 1-Benzyl-6-(3,4,5-trimethoxyphenyl)-1,3-dihydroimidazo[4,5-b]pyrazin-2-one; 6-(1H-Indol-5-yI)-1((S)-(–)-1-phenylethyl)-1,3-dihydroimidazo[4,5-b]pyrazin-2-one;
6-(3,5-Dimethylisoxazal-4-yl)-1-((S)-(–)-1-phenylethyl)-1,3-dihydroimidazo[4,5b]pyrazin-2-one;
3-[2-Oxo-3-((S)-(–)-1-phenylethyl)-2,3-dihydro-1H-imidazo[4,5-b]pyrazin-5-yl]-benzonitrile; 6-(3-Hydroxymethylphenyl)-1-((S)-(–)-1-phenylethyl)-1,3-dihydroimidazo[4,5-b]pyrazin-2-one;
6-(1H-Indo-2-yI)-1-((S)-(–)-1-phenylethyl)-1,3-dihydroimidazo[4,5-b]pyrazin-2-one;
1-Benzyl-6-pyridia-3-yI-1,3-dihydroimidazo[4,5-b]pyrazin-2-one;
1-Benzyl-6-(3,4-dimnethoxyphenyl)-1,3-dihydroimidazo[4,5-b]pyrazin-2-one;
1-Benzyl-6-(6-methoxypyridin-3-yl)-1,3-dihydroimidazo[4,5-b]pyrazin-2-one;
1-Benzyl-6-(3.methoxymethylphenyl)-1,3-dihydroimidazol[4,5-b]pyrazin-2-one;
6-(3-Acetylphenyl)-1-benzyl-1,3-dihydroimidazo[4,5-b]pyrazin-2-one;
1-Benzyl-6-(2,4-dimethoxyphenyl)-1,3-dihydroimidazo[4,5-b]pyrazin-2-one;
1-Benzyl-6-thiophen-3-yl-1,3-dihydroimidazo[4,5-b]pyrazin-2-one;
1-Benzyl-6-thiophen-2-yl-1,3-dihydroimidazo[4,5-b]pyraz.in-2-one;
1-Benzyl-6-(3-methoxyphenyl)-1,3-dihydroimidazo[4,5-b]pyrazin-2-one;
3-(3-Benzyl-2-oxo-2,3-dihydro-1*H-imidazo*[4,5-b]pyrazin-5-yl)-benzoic acid;
1-Pyridin-2-ylmethyl-6-(3,4,5-trimethoxyphenyl)-1,3-dihydroimidazo[4,5-b]pyrazin-2-one;
1-Pyridin-3-ylmethyl-6-(3,4,5-trimethoxyphenyl)-I,3-dihydro-imidazo[4,5-b]pyrazin-2-one;
1-Benzyl-6-(3,5-dimethoxyphenyl)-1,3-dihydro-imidazo[4,5-b]pyrazin-2-one;
5-(3-Benzyl-2-oxo-2,3-dihydro-1H-imidazo[4,5-b]pyrazin-5-yl)-2-methoxybenzoic acid;
1-Benzyl-6-(3-hydroxymethyl-4-methoxyphenyl)-1,3-dihydroimidazo[4,5-b]pyrazin-2-one;
5-(3-Benzyl-2-oxo-2,3-dihydro-1H-imidazo[4,5-b]pyrazin-5-yl)-2-hydroxybenzoic acid;
1-(3-Nitrobenzyl)-6-(3,4,5-trimethoxyphenyl)-1,3-dihydroimidazo[4,5-b]pyrazin-2-one;

1-(4-Chlorobenzyl)-6-(3,4,5-trimethoxyphenyl)-1,3-dihydroimidazo[4,5-b]pyrazin-2-one;

1-(3-Chlorobenzyl)-6-(3,4,5-trimethoxyphenyl)-1,3-dihydroimidazo[4,5-b]pyrazin-2-One;

1-(3-Methylbenzyl)-6-(3,4,5-trimethoxyphenyl)-1,3-dihydroimidazo[4,5-b]pyrazin-2-one;

1-(3-Fluorobenzyl)-6-(3,4,5-trimethoxyphenyl)-1,3-dihydroimidazo[4,5-b]pyrazin-2-one;

1-(3-Methoxybenzyl)-6-(3,4,5-trimethoxyphenyl)-1,3-dihydroimidazo[4,5-b]pyrazin-2-one;

1-Naphthalen-1-ylmethyl-6-(3,4,5-trimethoxyphenyl)-1,3-dihydroimidazo[4,5-b]pyrazin-2-one;

1-Benzo[1,3]dioxol-5-ylmethyl-6-(3,4,5-trimethoxyphenyl)-1,3-dihydroimidazo[4,5-b]pyrazin-2-one;

1-Indan-1-yl-6-(3,4,5-trimaethoxyphenyl)-1,3-dihydroimidazo[4,5-b]pyrazin-2one;

1-(2-Chlorobenzyl)-6-(3,4,5trimethoxyphenyl)-1,3-dihydroimidazo[4,5-b]pyrazin-2-one;

1-(4-Aminobenzyl)-6-(3,4,5-trimethoxypheflyl)-1,3-dihydroimidazo[4,5-b]pyrazin-2-one, 1-(3-Aminobenzyl)-6-(3,4,5-trimethoxyphenyl)-1,3-dihydroimidazo[4,5-b]pyrazin-2-one; or a pharmaceutically acceptable salt thereof.

5. A pharmaceutical composition comprising a compound of claim 1 and a pharmaceutically acceptable carrier.

6. A pharmaceutical dosage form comprising a pharmaceutically acceptable carrier and from about 0.5 mg to about 10 g of at least one compound of claim 1.

* * * * *

UNITED STATES PATENT AND TRADEMARK OFFICE
CERTIFICATE OF CORRECTION

PATENT NO. : 7,608,622 B2  Page 1 of 1
APPLICATION NO. : 11/233725
DATED : October 27, 2009
INVENTOR(S) : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 873 days.

Signed and Sealed this

Twelfth Day of October, 2010

David J. Kappos
*Director of the United States Patent and Trademark Office*